(12) United States Patent
Hainfeld et al.

(10) Patent No.: US 7,951,554 B2
(45) Date of Patent: *May 31, 2011

(54) KIT FOR ENZYMATIC DEPOSITION OF A METAL

(75) Inventors: James F. Hainfeld, Shoreham, NY (US); Wenqiu Liu, Dix Hills, NY (US)

(73) Assignee: Nanoprobes, Inc., Yaphank, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/707,575

(22) Filed: Feb. 17, 2010

(65) Prior Publication Data

US 2010/0221727 A1    Sep. 2, 2010

Related U.S. Application Data

(60) Division of application No. 11/714,682, filed on Mar. 5, 2007, now Pat. No. 7,691,598, which is a continuation-in-part of application No. 11/627,735, filed on Jan. 26, 2007, now Pat. No. 7,592,153, which is a division of application No. 10/658,609, filed on Sep. 8, 2003, now Pat. No. 7,183,072, which is a continuation-in-part of application No. 09/822,131, filed on Mar. 30, 2001, now Pat. No. 6,670,113.

(51) Int. Cl.
*C12Q 1/26* (2006.01)
(52) U.S. Cl. .......................................... 435/25; 435/975
(58) Field of Classification Search ................ 435/25, 435/975
See application file for complete search history.

(56) References Cited

U.S. PATENT DOCUMENTS

| 6,670,113 B2 * | 12/2003 | Hainfeld | 435/4 |
| 7,183,072 B1 * | 2/2007 | Hainfeld | 435/25 |
| 7,592,153 B2 * | 9/2009 | Hainfeld | 435/25 |
| 7,691,598 B2 * | 4/2010 | Hainfeld et al. | 435/25 |

* cited by examiner

*Primary Examiner* — Ralph Gitomer
(74) *Attorney, Agent, or Firm* — Klarquist Sparkman, LLP

(57) ABSTRACT

The present invention provides compositions, kits, assemblies of articles and methodology for carrying out processes that permit biological enzymes to act directly on metals and metal particles. In particular, the invention concerns using enzymes to selectively deposit metal to the vicinity of a target molecule. The invention also relates to linking of metals to enzyme substrates, control of enzymatic metal deposition and applications of enzymatic metal deposition to sensitively and selectively detect target molecules such as biomarkers in various biological samples, such as chromogenic immunohistochemical (IHC) detection in situ by using microscopy.

14 Claims, 11 Drawing Sheets

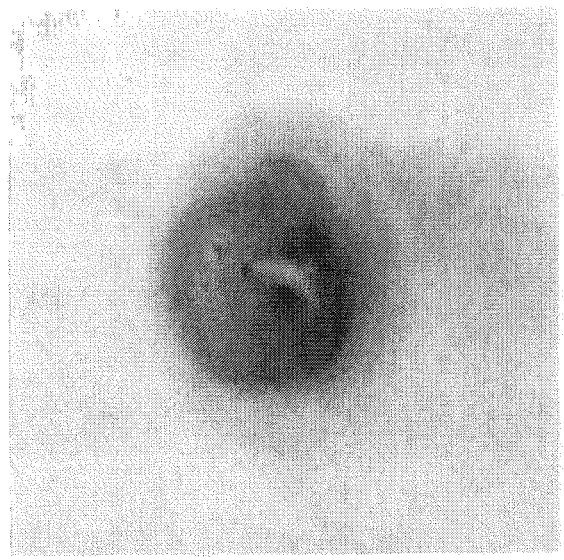 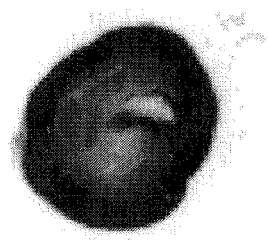
Fig. 1.
PRIOR ART
Fig. 2.

KIT FOR ENZYMATIC DEPOSITION OF A METAL

CROSS-REFERENCE TO RELATED APPLICATION

This application is a divisional application of Ser. No. 11/714,682 filed Mar. 5, 2007, now U.S. Pat. No. 7,691,598, which is a continuation-in-part application of U.S. patent application Ser. No. 11/627,735, filed Jan. 26, 2007, now U.S. Pat. No. 7,592,153 which is a divisional application of U.S. patent application Ser. No. 10/658,609, filed Sep. 8, 2003, now U.S. Pat. No. 7,183,072, issued Feb. 27, 2007, which is a continuation-in-part of U.S. patent application Ser. No. 09/822,131, filed Mar. 30, 2001, now U.S. Pat. No. 6,670,113, issued Dec. 30, 2003, the contents of which are incorporated by reference in their entirety.

BACKGROUND OF THE INVENTION

Enzymes: Their Function and Uses

Enzymes are proteins, usually derived from living organisms, that are also catalysts for various metabolic or chemical reactions. Enzymes are therefore essential to all life. Recently, enzymes have been isolated, studied, altered, combined with other agents, and used in various processes. Uses of purified enzymes range from laundry detergents (where enzymes break down stains) to pathological detection of cancer (where enzymes produce a visible color product on tumor cells in a biopsy). Enzymes can be immobilized, for example by attaching the enzyme to a surface such as a bead, flat surface, or electrode using adsorption or covalent linkage. Immobilization allows the enzymes to be held in place for handling or to sustain washing without being removed. Immobilized enzymes can be used as biosensors, for example to measure glucose levels for diabetics.

As previously stated, enzymes are catalysts. As used herein a "catalyst" is defined as a material that increases the rate of a chemical reaction but is not itself consumed. At the end of a reaction, the catalyst is present in its original form so that it may act on new substrates. As used herein "substrate" is defined as a chemical that an enzyme works on to produce a new chemical. A "substrate" is the input material or "reactant" in the reaction catalyzed by the enzyme. Catalysts function by binding the substrate chemical or chemicals, and either introduce bond strain or orient reactants, thus making a transition or reaction possible at lower temperature or energy. Since enzymes are catalysts, they lower the activation energy barrier between two chemical states. Enzymes can, for example, facilitate the conversion of one chemical compound into another, or facilitate a reaction between chemicals. Without enzymes, reactions would be slow or, for most practical purposes, would not occur. This lowering of the activation energy barrier is one reason enzymes are required for living organisms. Enzymes control most body processes, and even cancer involves improper levels of certain enzymes regulating cell growth and death.

Enzymes fall into various classes relating to the type of reaction they catalyze, for example: oxido-reductases (such as dehydrogenases, oxidases); hydrolases (such as esterases, lipases, phosphatases, nucleases, carbohydrases, proteases); transferases; phosphorylases; decarboxylases; hydrases; and isomerases. Although enzymes within living cells act on specific compounds, it has been found that many enzymes will also act on other related compounds. Enzymes have also been found to perform similar reactions on synthetic or man-made substrates.

One use of enzymes is to perform reactions that convert a substrate into a detectable product. For example, a nonfluorescent compound may be converted into a fluorescent compound by cleavage of a particular bond using an enzyme. Alternatively, a colorless compound may be converted into a colored one by using an enzyme. Other uses of enzymes are deposition of a colored or otherwise detectable organic substrate from solution onto a solid support. This may be done by using an enzyme to make a soluble starting compound insoluble. Alternatively, enzymes can make a starting compound reactive, such as by forming a free radical thereof. The free radical subsequently reacts with, and binds to, the surrounding material. A useful embodiment of this technology is the ELISA test (Enzyme Linked ImmunoSorbant Assay), where, for example, an antigen is adsorbed to a solid support, such as a plastic microtiter plate well. To determine if an antibody to the antigen is present in a patient's serum, the serum is incubated in the coated well. If the antibody is there, it will bind to the immobilized antigen. After washing, a solution containing an anti-human antibody linked to the enzyme alkaline phosphatase is applied. The anti-human antibody will attach to any bound primary antibodies present. After washing, a substrate is applied, and if the alkaline phosphatase is present it will convert the colorless BCIP (5-bromo-4-chloro-3-indolyl phosphate) into a soluble color, which can then be measured spectrophotometrically. The amount of colored product produced is correlated with the amount of antibody in the serum, providing a quantitative measurement.

A number of significant advantages are gained by using enzymes for detection. These advantages include: a) Amplification: since the enzyme is a catalyst, and does not get used up in the reaction, and it can be used over and over. As more substrate is added more detectable product is produced. Except for practical limitations, the amount of product produced could be limitless. b) Linearity: the detectable product produced from the reaction of enzyme and substrate follows enzyme kinetics for that enzyme, and these can be relatively linear within some range. Even if the particular enzyme kinetics is not linear, the reaction may be calibrated. c) Selectivity: enzymes are usually very selective for the type of reaction and stereochemistry involved. Thus unwanted interferences may be reduced. d) Low background: if the conversion of the substrate to a colored or otherwise altered compound is negligible without the enzyme, then the background can be very low.

Enzymes themselves may be modified, for example, by genetic engineering or chemical modification, to produce alterations in specificity or reactivity, or to impart other characteristics, such as reduced immunogenicity (if the enzyme is to be used in vivo), or improved stability (for better shelf life or environmental tolerance).

A further expansion of the enzyme field relates to the use of unconventional material as biological catalysts, either proteins that are not normally enzymes, or non-protein material; for example, catalytic antibodies have been described.

Enzyme Substrates for Use in Detection Systems

The types of enzyme substrates popularly used for sensitive detection are typically colorimetric, radioactive, fluorescent or chemiluminescent. Conventional colorimetric substrates produce a new color (or change in spectral absorption) upon enzyme action. This type of detection is advantageous in that the colors produced are easily detected by eye or with spectral equipment. The cost of equipment for detection is also generally less than with other methods; for example in pathology, the brown color produced by the enzyme horseradish. peroxidase (HRP) acting on 3,3'-diaminobenzidine (DAB), requires only a simple bright field light microscope for observation of biopsied sections. A disadvantage of these colorimetric substrates is that they are generally of lower sensitivity than other enzyme methods.

Conventional radioactive substrates can enzymatically release or fix radioactivity for measurement. Although sensitive, this type of detection is becoming less popular due to the risks of handling and disposing of radioactive material, and since other methods now rival or exceed its sensitivity. Radioactive labeling for histochemical uses and autoradiography, typically require months to expose films, due to low specific activity, which is another disadvantage.

Conventional fluorescent substrates are popular since they are reasonably sensitive, generally have low backgrounds, and several differently colored fluorophores can be used simultaneously. A number of drawbacks, however, come with use of fluorescent substrates. Fluorescence requires expensive fluorescence optics, light sources and filters; by comparison, standard bright field microscopes are significantly less expensive. Fluorescence fades upon observation, sample storage or even exposure to room lights, thus making permanent or quantitative data difficult to achieve. Autofluorescence (fluorescence coming from certain compounds found naturally in many living organisms) from cells and other molecules can interfere with the test result. Standard tissue stains (such as nuclear fast red, hematoxylin, and eosin) cannot be seen simultaneously with the very different optics and illumination required for fluorescence detection, thus making visualization of landmarks of a tissue difficult. The standard viewing of tissues is done with bright field optics using colored stains and a standard microscope. Unfortunately, fluorescence is viewed using different illumination and sharp bandpass filters, so that only the fluorescent label is visible, and the general view of the stained tissue is not simultaneously available.

Chemiluminescence is based upon use of substrates that have sufficiently high chemical bond energies so that when the bonds are broken by an enzyme, energy is released in the form of visible light. This method has gained popularity due to the low background and very high sensitivity obtainable using photomultipliers, avalanche diodes or other sensitive light detectors. Alternatively photographic film can be used as a detection means. Chemiluminescence has a number of disadvantages. Detection requires expensive equipment or necessitates film development. The sample is not a permanent record, since the emitted light must be collected over time. Sensitive detection often requires lengthy light integration times of hours or even a day. Standard stains (such as nuclear fast red, hematoxylin, and eosin) cannot be seen simultaneously, thus making visualization of landmarks of a tissue difficult, for example. Only the emitted light from points in the specimen can be seen.

Additionally, all of the conventional detection schemes have some practical limitations for sensitivity. One limiting factor is the background, or non-specific signal generated. The background noise can come from various sources. For example with fluorescence detection the background can come from autofluorescence, fluorescent molecules that adhere to non-specific sites, light reflection off structures and other sources. Another limitation on detection method sensitivity is the amount of signal produced. For example, if an enzyme is used that has a low turnover, and produces only relatively few products, these few products will be harder to detect, and sensitivity will be worse than if a more efficient enzyme producing more products was used.

As mentioned earlier, since an enzyme is a catalyst and is not used up during reaction it can be fed more substrate, ideally forming product indefinitely. This provides a form of amplification. Of course there are practical limitations to enzyme amplification, such as the enzyme losing activity, the long times necessary to accumulate product, side reactions or other sources of background limit detection. Further, at some point the product produced may interfere with enzyme activity, either by shifting the reaction equilibrium, depositing products so as to impede flow to the active site of the enzyme or otherwise inhibiting the enzyme.

Although a number of enzyme based assays have been developed, one that is gaining popularity for sensitive detection is CAtalyzed Reporter Deposition (CARD), also known as Tyramide Signal Amplification (TSA, a trademark of New England Nuclear Corp, subsidiary of Perkin Elmer). In one variation of this method (there are several variations) a biotinylated antibody or nucleic acid probe detects the presence of a target by binding thereto. Next a streptavidin-peroxidase conjugate is added. The streptavidin binds to the biotin. Streptavidin is a protein isolated from the bacterium *Streptomyces*. Biotin is an organic compound having the formula $C_{10}H_{16}N_2O_3S$. A substrate of biotinylated tyramide (tyramine is 4-(2-aminoethyl)phenol) is used which presumably becomes a free radical when interacting with the peroxidase enzyme. The phenolic radical then reacts quickly with the surrounding material, thus depositing or fixing biotin in the vicinity. This process is repeated by providing more substrate (biotinylated tyramide) and building up more localized biotin. Finally, the "amplified" biotin deposit is detected with streptavidin attached to a fluorescent molecule. Alternatively, the amplified biotin deposit can be detected with avidin-peroxidase complex, that is then fed 3,3'-diaminobenzidine to produce a brown color. It has been found that tyramide attached to fluorescent molecules also serve as substrates for the enzyme, thus simplifying the procedure by eliminating steps. Although this type of assay has been used quite successfully, it has several drawbacks, including: expense of reagents, insufficient amplification, background problems, localization at the ultrastructural level (using electron microscopy) can be diffuse, and the limitations using fluorophores or chromophores mentioned previously.

Enzyme Biosensors

As used herein a biosensor is a device that uses biological materials to monitor the presence of a selected material, or materials, in a medium. Enzymes can be used in biosensor applications. Redox (reduction-oxidation) enzymes are used to generate an electrical signal, since electrons are transferred in redox reactions. Various other enzymes have been used in biosensors, and are selective for the following analytes, including use of beta-glucosidase to detect amygdalin, asparaginase for asparagine, cholesterol oxidase for cholesterol, chymotrypsin for esters, glucose oxidase for glucose, catalase for hydrogen peroxide, lipase for lipids, penicillinase for penicillin G, trypsin for peptides, amylase for starch, invertase for sucrose, urease for urea, and uricase for uric acid. Generally, biosensors achieve signal transduction using one of three approaches: amperometric, potentiometric and optical.

Amperometric biosensors work by enzymatically generating a current between two electrodes. The simplest design is based on the Clark oxygen electrode. The Clark oxygen electrode has a platinum cathode and a silver/silver chloride anode. Oxygen is reduced at the platinum cathode to water, and silver is oxidized to silver chloride at the anode. The rate of electrochemical reaction for the electrode is therefore dependent on the oxygen content of the solution. In a glucose monitor, glucose is a substrate for the immobilized glucose enzyme oxidase, which oxidizes glucose (consuming oxygen) to produce gluconic acid and hydrogen peroxide. This change in oxygen content alters the electrode current.

A variation on the above method measures the hydrogen peroxide produced by the enzymatic oxidation of glucose by making platinum the anode, and biasing it to 0.7 volts such that the hydrogen peroxide is oxidized back to oxygen, producing 2 electrons. Although the glucose oxidase is selective for glucose, and does not react with the closely related sugar fructose, some other molecules frequently found in the blood, either products of normal metabolism (e.g. uric acid) or drugs/medicaments taken orally (e.g. paracetamol or Vitamin C), can also break down directly and electrochemically at the electrode, bypassing the enzyme and giving a spurious signal. Similarly, the enzyme/device interface in other types of known biosensors is often prone to similar non-specific signals. In another variation redox enzymes may be coupled to other enzymes that interact with a specific substrate of interest to produce a product, the product then driving the redox enzyme.

Potentiometric biosensors are usually based on ion-selective electrodes. Such devices measure the release or consumption of ions during a reaction; the simplest potentiometric biosensor is based on a pH-probe. Glucose oxidase, for example, catalyzes the oxidation of glucose to gluconate, producing $H^+$ ions and hydrogen peroxide. The $H^+$ ions are then sensed by the pH probe. Detection is usually in the $10^{-4}$ to $10^{-2}$M region, and therefore the above method generally lacks the accuracy and precision required for many analytes.

Optical biosensors have two common designs. In a first design light absorption is measured. An example is light absorption through a dye having a changed color that is the result of an enzyme driven pH change. A second design is based on measuring luminescence. An example is use of the enzyme firefly luciferase that reacts with ATP (adenosine triphosphate) and oxygen to produce AMP (adenosine monophosphate), $PP_i$ (inorganic pyrophosphate), oxyluciferin, $CO_2$ and a photon of light. This reaction can be coupled to any enzyme that produces or consumes ATP.

Metals and Enzymes

Some enzymes contain essential metal ions that are bound and required for activity. The metal ions aid in constraining the substrate for the reaction, but are not themselves consumed or deposited, they are part of the catalyst. Examples of enzymes that contain or require metal ions as cofactors are: alcohol dehydrogenase, carbonic anhydrase, and carboxypeptidase, which all require zinc ions; some phosphohydrolases and phosphotransferases require magnesium ions, arginase requires manganese ions; cytochromes, peroxidase, catalase, and ferredoxin contain iron ions; tyrosinase and cytochrome oxidase contain copper ions, pyruvate phosphokinase requires potassium ions, and plasma membrane ATPase requires sodium ions. However, these metal ions do not serve as substrates, are not linked to substrates and do not deposit as metal.

A very few metal ions are known to interact with enzyme reaction products. For example, the enzyme horseradish peroxidase can produce a diaminobenzidine (DAB) polymer; Nickel or cobalt ions complex with the DAB polymer to give the polymer a darker color. Unfortunately, this use has not been widely employed since the background goes up substantially, and little improvement in signal-to-noise ratio is generally found. Similarly osmium tetroxide can be added to the DAB polymer after it is formed. The osmium tetroxide reacts with the DAB product and leads to incorporation of the heavy metal, making the DAB deposit more visible in the electron microscope.

SUMMARY OF THE INVENTION

The present invention provides innovative compositions, kits, assembles of articles and methodology for carrying out processes that permit enzymes to act directly on metals and metal particles. In particular, the invention relates to use of enzymes to selectively deposit metal to the vicinity of a target molecule. The invention also relates to linking of metals to enzyme substrates, control of enzymatic metal deposition and applications of enzymatic metal deposition to sensitively and selectively detect target molecules such as biomarkers in various biological samples, such as chromogenic immunohistochemical (IRe) detection in situ by using bright field light microscope. The biological samples include, but are not limited to, cell cultures or mixtures, cytological specimens, tissue slices or sections, biopsies, and samples contains nuclei of cells, in a form of liquid, suspension, solid and immobilized to a solid support such as a slide.

An object of the invention is to utilize enzymes to accumulate and/or deposit metal particles.

Another object of the invention is to utilize enzymes to act upon suitable metal ion substrates resulting in metal deposition.

Yet another object of the invention is to utilize enzymes to act upon suitable metal ion substrates to produce detectable changes.

Still another object of the invention is to utilize enzymes to act upon suitable metal ion substrates to produce quantifiable changes.

A further object of the invention is to utilize enzymatic reactions that act on ligands attached to metal particles to produce detectable changes.

A still further object of the invention is to utilize enzymes to act on substrates liganded to metal surfaces to produce quantifiable changes.

One embodiment of the present invention describes a method for using enzymes to selectively catalyze metal deposition. As used herein "metal deposition" is defined as a buildup or accumulation of metal (metallic elements in the zero oxidation state) in the vicinity of the enzyme. Typically, metal deposition will start within a distance of about 1 micron from the enzyme. Naturally as metal deposition continues the metal accumulation may extend beyond this distance. Two aspects are disclosed. In a first aspect, metal nanoparticles having a diameter in the range of about 0.8 to 50 nm are linked to, or contain, compounds that are acceptable enzyme substrates. When the enzyme deposits the substrate compound, the metal particles are co-deposited. In a second aspect enzymes, or modified enzymes, are used to directly reduce metal ions to deposit metal. As used herein "modified enzymes" in this specific context are defined to be enzymes that are pretreated with a solution of metal ions before a reducing and oxidizing agent are added. Extensions of the above embodiments included as inventive aspects include electrochemical or electroless plating of the same or a different metal over the metal particle or deposit.

In other embodiments of the present invention various applications for using the enzymatically deposited metals are disclosed. For example, the inventive enzymatically deposited metals may be used for highly sensitive gene detection, sensitive immunodetection, novel biosensor designs, bacterial detection, remediation and nanofabrication of novel materials.

The novel forms described for metals, and/or metal-ligand complexes, participating as substrates for enzymes lead to very distinct advantages over known methods of detection. Some of these advantages are listed below.

No harmful radioactivity need be handled or disposed of to achieve comparable or better sensitivity in assays. No lengthy time of exposure is needed (autoradiograms can take several months to expose). No film, film processing or film chemicals are required.

Gold nanoparticles have extinction coefficients about 1,000 times higher than highly colored compounds or fluorophores. Therefore, their use substantially increases sensitivity.

No expensive fluorescent optics, light sources or filters are required. Site-specific and selective deposition of elemental metal in the targeted site or molecules not facilitates chromogenic detection of the signals, allows cell morphology and in situ hybridization (ISH) signal to be viewed at the same time, and provides accurate results using standard equipment, such as bright field-microscopes. There is no fading of the sample upon observation or storage or exposure to room lights. Autofluorescence from cells and other molecules does not create any interference. Standard stains (such as nuclear fast red, hematoxylin and eosin) can be used and seen simultaneously with the enzyme deposited metals, making visualization of landmarks of a tissue simple.

In one aspect, the enzymatic metal deposition of the invention allows deposition of silver metal in the presence of an enzyme and activating agents with high sensitivity combined with high resolution and minimal background for chromogenic in situ hybridization (CISH) detection, and visualization in the conventional bright field microscope without the need for oil immersion. Such an assay is herein termed as "Silver In Situ Hybridization" (SISH). In particular, the enzymatic metal deposition of the invention allows detection of a single copy of a target gene in a chromosome by a conventional bright field microscope with requiring oil immersion. The invention also enables detection of gene copies with a resolution that allows for individual enumeration of signals, such as discrete metal deposit dots for individual gene copies. In a variation of the embodiment, the invention allows for detection of at least 2, 3, 4, 5, 6, 7 or 8 copies of a target gene per nucleus, such as HER2 gene in human chromosome 17, as discrete metal deposit dots.

In one embodiment, a method is provided for detecting a target molecule in a test sample. The method comprises: binding an enzyme to the target molecule in the test sample; combining an enzyme with metal ions, an oxidizing agent and a reducing agent; incubating the enzyme with the metal ions in the presence of the oxidizing agent and the reducing agent, whereby the metal ions are reduced to elemental metal; depositing the elemental metal in the vicinity of the enzyme; and determining the presence, amount or level of the deposited metal in the vicinity of the enzyme.

According to the embodiment, the step of binding includes binding the enzyme to the target molecule via a primary antibody that specifically binds to the target molecule, and a secondary antibody that is conjugated with the enzyme and binds to the primary antibody.

Optionally, the step of binding includes binding the enzyme to the target molecule via a nucleic acid probe that specifically hybridizes to the target molecule and is labeled with detectable marker, wherein the enzyme binds to the detectable marker via an antibody that specifically binds to the detectable marker. Examples of the detectable marker include but are not limited to biotin, digoxingenin, dinitrophenyl (e.g., 2,4-dinitrophenyl (DNP), a radio-isotope or a fluorescent label such as fluorescein isothiocyanate (FTIC), Texas Red, rhodamine and Cy5. The enzyme may bind to the detectable marker via a primary antibody that specifically binds to the detectable marker, and a secondary antibody that is conjugated with the enzyme and binds to the primary antibody.

The target molecule may be a target gene, gene product, or genome. For example the gene is a gene encoding an angiogenic growth factor receptor selected from the group consisting of receptor for fibrin (VE-cadherin), receptors for VEGF (Flt1 and KDR), receptor for VEGF-C and VEGF-D (Flt4), receptor for VEGF-165 (NP-1 and NP-2), receptors for angiopoeitin-1, -2, -3, and -4 (Tie 1 and Tie 2), receptors for FGF (FGF-R1, -R2, -R3 and -R4), receptor for PDGF (PDGF-R), receptor for ephrine A1-5 (Eph A1-8), and receptor for ephrine B1-5 (Eph B1-8). Optionally, the target gene is a gene encoding a receptor tyrosine kinase selected from the group consisting of epidermal growth factor receptors (EGFR), platelet-derived growth factor receptors (PDGFR), vascular endothelial growth factor receptors (VEGFR), nerve growth factor receptors (NGFR), fibroblast growth factor receptors (FGFR), insulin receptors, ephrin receptors, Met, and Ror. Examples of the epidermal growth factor receptor include HER1, HER2/neu (or HER-2/neu), HER3, or HER4. Also optionally, the target gene encoding a non-receptor tyrosine kinase selected from the group consisting of Kit (such as c-Kit), Src, Fes, JAK, Fak, Btk, Syk/ZAP-70, and Abl.

Also according to the embodiment, the method further comprises: comparing the presence, amount or level of the deposited metal with that of a reference sample; and determining a disease status of a patient from whom the test sample is derived.

The reference sample may comprise a cell or tissue from a normal, healthy tissue, or from another disease tissue with known disease status, such as a breast tumor tissue.

The disease status may be disease determination or classification, prognosis, drug efficacy, patient responsiveness to therapy, whether adjuvant or combination therapy is recommended, or likelihood of recurrence of disease. Examples of the disease include but are not limited to benign tumors, cancer, hematological disorders, autoimmune diseases, inflammatory diseases, cardiovascular diseases, nerve degenerative diseases and diabetes.

Optionally, the disease status is patient responsive to therapy. For example, the disease is breast cancer; the therapy is trastruzumab or HERCEPTIN therapy; and the target molecule is HER2/neu gene or protein. For another example, the disease is gastrointestinal stromal tumor (GIST); the therapy is imatinib mesylate or GLEEVEC therapy; and the target molecule is c-Kit gene or protein.

In another embodiment, a method of depositing elemental metal in the vicinity of an enzyme is provided which can used for many applications described herein. The method comprises: combining an enzyme with metal ions, an oxidizing agent and a reducing agent, wherein the weight ratio of the metal ions to the reducing agent ranges from 1:5 to 5:1, and the weight ratio of the reducing agent to the oxidizing agent ranges from 1:10 to 10:1; incubating the enzyme with the metal ions in the presence of the oxidizing agent and the reducing agent, whereby the metal ions are reduced to elemental metal; and depositing the elemental metal in the vicinity of the enzyme, wherein the metal ions are selected from the group consisting of silver, gold, iron, mercury, nickel, copper, platinum, palladium, cobalt, iridium ions and a mixture thereof.

According the present invention, examples of the metal ions include but are not limited to silver, gold, iron, mercury, nickel, copper, platinum, palladium, cobalt, iridium ions and a mixture thereof. Preferably, the metal ions are silver ions.

Examples of the enzyme include but are not limited to oxido-reductases (such as dehydrogenases, oxidases); hydrolases (such as esterases, lipases, phosphatases, nucleases, carbohydrases, proteases); transferases; phosphorylases; decarboxylases; hydrases; and isomerases. Preferably, the enzyme is peroxidase. More preferably, the enzyme is horseradish peroxidase. The peroxidase can utilize a colorless organic substrate capable of being converted by the peroxidase to a colored substrate. Examples of the colorless organic substrate is 3,3'-diaminobenzidine or 5-bromo-4-chloro-3-indolyl phosphate. The enzyme may be optionally conjugated to streptavidin, or to an antibody.

The oxidizing agent may be an oxygen-containing oxidizing agent, such as hydrogen peroxide.

Examples of the reducing agent include but are not limited hydroquinone, a hydroquinone derivative, n-propyl gallate, 4-methylaminophenol sulfate, 1,4 phenylenediamine, o-phenylenediamine, chloroquinone, bromoquinone, 2-methoxyhydroquinone, hydrazine, 1-phenyl-3-pyrazolidinone and dithionite salts.

According to the present invention, preferably the enzyme is a peroxidase; the metal ions are in a form of silver acetate; the oxidizing agent is hydrogen peroxide; and the reducing agent is hydroquinone. The weight ratio of silver acetate to hydroquinone ranges from about 1:2 to about 4:1, optionally from about 1:1 to about 3:1, or optionally from about 1:1 to about 2:1. The weight ratio of hydroquinone to hydrogen peroxide ranges from 1:2 to 6:1, optionally from about 1:1 to about 4:1, or from about 1:1 to about 3:1, or optionally about 1:1 to about 2:1.

Optionally, the steps of combining and incubating includes: i) combining the enzyme with the metal ions; ii) incubating the mixture of the enzyme and the metal ions at about 4-40° C. for about 1-10, 2-8 or 3-5 minutes; iii) combining the incubated mixture of the enzyme and the metal ions with the reducing agent and the oxidizing agent; and iv) incubating the mixture of the enzyme, the metal ions, the reducing agent and the oxidizing agent at about 4-40° C. for about 1-30, 2-20, 5-15, or 8-14 minutes.

Optionally, the steps of combining and incubating includes i) combining the enzyme with the metal ions; ii) incubating the mixture of the enzyme and the metal ions at about 4-40° C. for about 1-10, 2-8 or 3-5 minutes; iii) adding the reducing agent to the mixture of step ii); iv) adding the oxidizing agent to the mixture of step iii), and incubating at about 4-40° C. for about 1-30, 2-20, 5-15, or 8-14 minutes.

The method optionally further comprises: stopping the deposition of the elemental metal to the vicinity of the enzyme after a certain period of time. The step of stopping may include washing away residual metal ions from the enzyme. Optionally, the step of stopping includes rinsing the enzyme with a solution selected from the group consisting of a solution combining sodium thiosulfate and ammonium chloride, a solution of potassium thiocyanate, a solution combining potassium ferricyanide and sodium thiosulfate, a solution of potassium ferricyanide, a solution of sodium thiosulfate, and a solution of sodium periodate.

The method optionally further comprises: detecting the elemental metal deposited in the vicinity of the enzyme by automatallography or by bright field light microscopy.

The present invention also provides a kit, comprising: metal ions selected from the group consisting of silver, gold, iron, mercury, nickel, copper, platinum, palladium, cobalt, iridium ions and a mixture thereof; an oxidizing agent; a reducing agent; and an enzyme. Preferably, the weight ratio of the metal ions to the reducing agent ranges from 1:5 to 5:1, and the weight ratio of the reducing agent to the oxidizing agent ranges from 1:10 to 10:1.

The kit may further comprise a binding moiety that binds to a target molecule, such as an antibody, antibody fragments, peptide, nucleic acids, nucleic acid probes, carbohydrates, drugs, steroids, products from plants, animals, humans and bacteria, and synthetic molecules, where each member has an affinity for binding to the target molecule. For example, the target molecule is a target gene or genome and the binding moiety is a nucleic acid probe that binds to the target gene or genome. The enzyme binds to the target molecule via a primary antibody that binds to the target molecule, or via a primary antibody that binds to the binding moiety. Optionally, the enzyme is conjugated to a secondary antibody that binds to the primary antibody. Preferably, the enzyme is peroxidase; the metal ions are silver ion; the oxidizing agent is hydrogen peroxide; and the reducing agent is hydroquinone.

The kit may further comprise instruction for performing a process of depositing elemental metal in the vicinity of the enzyme.

The invention disclosed herein utilizes an enzyme reaction for deposition or product formation. The deposition rates are determined by enzyme kinetics, which result in linear or easily calibrated rates of reaction. This makes the invention much more suitable for quantitative detection than conventional autometallographic methods of depositing metal on nucleating particles. Additionally the invention does not suffer from irregular rates of deposition from particle to particle as is known to occur with conventional autometallographic methods.

The present invention has an inherent amplification step since an enzyme catalyst is used. Thus the invention can provide more sensitive detection than is possible with non-enzymatic methods, such as direct immunolabeling with a fluorophore or chromophore.

Compared with, for example, deposition of an organic molecule; enzymatic metal deposition makes possible many additional detection methods including by x-rays, electron microscopy, electrochemical, optical, magnetic, and many others. Many of the additional test methods useful with enzymatic metal deposits are exceedingly sensitive, and permit assays more sensitive and/or rapid than is possible with conventional test methods.

In particular, the enzymatic metal deposition method of the invention can be used for detection of a wide variety of biological molecules as biomarkers for research, diagnosis, prevention and treatment of diseases and conditions. For example, the inventive method can be used to determine a disease status of a mammal, preferably a human subject, by detecting the level of the biomarker in a sample derived from the mammal. Such "disease status" may relate to disease determination or classification, prognosis, drug efficacy, patient responsiveness to therapy (the so-called "targeted therapy"), whether adjuvant or combination therapy is recommended, likelihood of recurrence of disease, or the like.

In general, the material of the invention may be alternately formulated to comprise, consist of, or consist essentially of, any appropriate components herein disclosed. The material of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the results of a conventional blot test showing color developed by peroxidase acting on DAB (3,3'-diaminobenzidine). One microliter containing one microgram of the enzyme horseradish peroxidase was applied to a piece of white nitrocellulose membrane and permitted to dry. Next, 1 ml of 50 mM TRIS buffer, pH 7.6 was applied containing 10 microliters of 10% DAB and 10 microliters of 3% hydrogen peroxide. Note that when a hydrogen peroxide concentration is used in this application, that concentration is the final or absolute concentration of hydrogen peroxide in the solution. In a few minutes, a brown color appeared over the area containing the peroxidase (the central spot). However, some background is apparent surrounding this spot, as evidenced by the brown color on the rest of the membrane. The blot was washed with water to stop the reaction. The blot is magnified 7 times.

FIG. 2 illustrates the results of a blot test incorporating one aspect of the invention showing a signal developed by enzyme metal deposition. Similarly to the procedure used in FIG. 1, one microliter containing one microgram of the enzyme horseradish peroxidase was applied to a piece of white nitrocellulose membrane and permitted to dry. Next the blot was incubated with 1 ml of 0.2% silver acetate in water for 3 minutes. The blot was washed twice with water and a 1 ml solution (comprising 2.5 mg/ml hydroquinone, 1 mg/ml silver acetate, and 0.06% hydrogen peroxide in 0.1 M citrate buffer, pH 3.8) was applied. In under a minute, a black colored silver metal deposit appeared over the area containing the peroxidase. The blot was washed with water to stop the reaction. Compared to the conventional reaction shown in FIG. 1, the enzyme metal deposition of this invention shows a much denser and more visible product, and shows no background deposition outside the enzyme area. The blot is magnified 7 times.

DETAILED DESCRIPTION OF PREFERRED EMBODIMENTS

Figure 3:
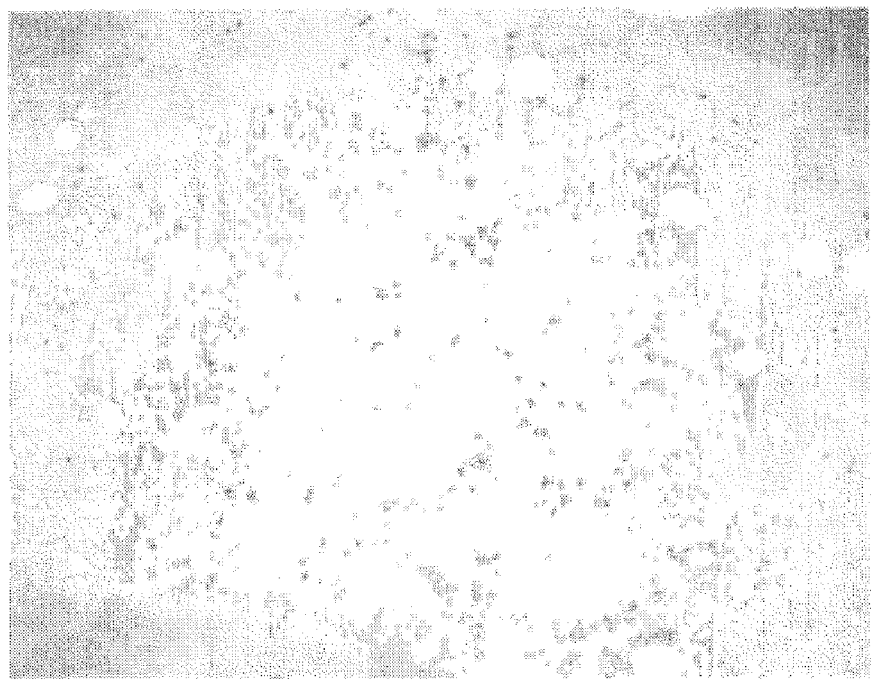
FIG. 3 illustrates the results of a conventional immunostaining test using an antibody, peroxidase, and the substrate AEC (3-amino-9-ethylcarbazole). Human colon carcinoma tissue was fixed in formalin and embedded in paraffin. Next it was sectioned and placed on glass slides for the light microscopy. Sections were deparaffinized with toluene, and rehydrated through successive washes in 100%, 95%, 80%, 70% ethanol, and finally phosphate buffered saline (PBS: 0.01M sodium phosphate, 0.14M sodium chloride, pH 7.4). Endogenous peroxide was quenched by incubating with 2 drops of 3% hydrogen peroxide for 5 minutes, followed by washing in PBS. Sections were then incubated with a biotinylated monoclonal antibody to an antigen in the section for 1 hour at room temperature. After washing with PBS, the sections were next incubated with a streptavidin-peroxidase conjugate for 20 min. After washing with PBS, the substrate AEC was applied in 50 mM acetate buffer, pH 5.0 containing 0.03% hydrogen peroxide. A reddish color developed over certain areas targeted by the monoclonal antibody. The slide was washed with water to stop the reaction after 20 min. Full width of bright field light micrograph shown is 250 microns.

One aspect of the invention relates to constructing substrates for enzymes that contain metal particles in the range of about 0.8 to 50 nm in diameter. It should be noted that the terms metal particles and metal clusters are interchangeably used to refer to metal particles. This concept has not been affected nor is it deemed possible by those skilled in the art for several reasons. Enzymes are highly specific; for example, glucose oxidase will accept glucose and not the closely related sugar fructose. Additionally enzymes are stereospecific. Coupling a "large" metal sphere (large in comparison to the substrate, for example the metal sphere is sometimes twice the substrate size) to the substrate may alter the substrate structure or present steric hindrances that would interfere with enzyme activity. The accepted approach is to enzymatically deposit a small molecule, such as biotin, then detect this with streptavidin which is pre-coupled to a gold particle.

Surprisingly, the inventor has discovered that some metal particle-enzyme substrates, are accepted by some enzymes, and result in specific deposition of metal particles. One mechanism of metal particle deposition is believed to include oxidation or reduction of the substrate forming a species that polymerizes and accumulates creating an insoluble mass. In another possible mechanism, bonds in the substrate are broken or made which release or alter solubilizing moieties; the substrate is converted from a soluble compound into an insoluble material, which then builds up around the enzyme. In a further possible mechanism the enzyme creates a free radical on the substrate, making it highly reactive; the free radical substrate attaches to solid material around the enzyme and is covalently fixed in place. Continued enzyme action adds more product, thus building up a deposit.

This discovery, which as explained above is contrary to both skilled opinions and current practices, has significant advantages. For example, directly depositing metal particles eliminates steps in the existing method of biotin deposition followed by streptavidin-gold (or other similar processes), thus reducing time and costs. It also brings the metal particles closer to the enzyme for better spatial resolution. Improved spatial resolution is important for electron microscopy localizations and nanofabrication. Since the metal is deposited directly, the efficiency and occupancy of deposition at enzymatic sites is improved. For electrochemical applications, tunneling and charge conduction is highly dependent on particle spacing, and the new method permits particles to be deposited so that useful conduction may be achieved. Hence, a number of significant benefits are achieved by this aspect of the invention.

As an example, gold particles in the range of about 0.8 to 50 nm may be synthesized by reduction of gold salts or gold compounds. For example, $HAuCl_4$ at 0.01% by weight in water is reduced by 2 milliMolar sodium citrate in boiling water to produce approximately 10 nm gold particles. By changing the amount of citrate, different sized gold particles may be produced. Other reducing agents (besides citrate) and recipes are known for producing metal particles in the size range of about 0.8 to 50 nm. An organic layer or shell may be bound to the metal particle surface, typically consisting of thiol compounds, phosphines, polymers, proteins or other compounds. The use of the term organic layer or shell is also meant to include partial or incomplete coverage of the metal particle surface. Some metal particles have these organic coatings attached by adsorption, whereas others are attached by covalent bonding between surface metal atoms and, for example, sulfur or phosphorus atoms.

Various methods were found to attach the enzyme substrate to the metal particle. In one method reactive groups (e.g., amines) of the metal particle organic layer are used to crosslink to the enzyme substrate. For example, a gold particle stabilized with phosphines containing at least one aminophoshine may be coupled via the aminophosphine to 3,3' diaminobenzidine. The coupled gold particle-3,3'-diaminobenzidine then becomes a substrate for horseradish peroxidase, resulting in deposition of gold particle.

In another method the substrate is incorporated directly into the metal particle organic layer. Gold particles were formed from gold salts reduced with sodium borohydride in the presence of glutathione and 3,3'-diaminobenzidine (DAB), then purified by column chromatography to remove unreacted starting materials. The glutathione and DAB are incorporated into the gold particles. These gold particles were found to be deposited by horseradish peroxidase in the presence of hydrogen peroxide. Alternatively gold particles can be made from gold salts reduced with sodium borohydride in the presence of glutathione and 4-hydroxythiophenol, then purified by column chromatography to remove unreacted starting materials. The gold particles with incorporated substrate so produced were found to be deposited by horseradish peroxidase in the presence of hydrogen peroxide.

In a further method, gold particles stabilized by thioglucose were found to be deposited from solution by horseradish peroxidase if hydroquinone and hydrogen peroxide were included in the solution. These deposited gold particles contained glucose and were also demonstrated to have activity with the enzyme glucose oxidase.

Another aspect of the invention is the enzymatic alteration of the metal particle coating. This aspect of the invention is applicable even if the metal particles are already deposited and remain deposited, or become soluble, or if the particles are in solution and remain in solution after the enzymatic reaction. For example, a phosphatase will cleave a phosphate group linked to the surface of a gold cluster or particle, thus changing its net charge. The gold particles may remain in solution, but will now move differently in an applied electric field, and therefore the gold particles will electrophorese differently. Since the gold particles are highly visible and detectable, a sensitive assay of phosphatase activity may be achieved using this phenomenon.

Another example of a novel enzymatic alteration of a metal particle is the proteolytic cleavage of a protein or peptide bound to a metal particle. Upon action of, for example, proteinase K or trypsin, some of the protein shell attached to the metal particle was cut by the enzyme and released, resulting in alteration of the absorption spectrum or in some cases aggregation of the metal particles.

Another aspect of the invention is expansion from use with metal particles to metal surfaces generally. Most of the ligands that stabilize and bind to metal particles also adhere to metal surfaces. As used herein "ligand" is defined to be a material that is attached to a metal particle or metal surface. As previously discussed the same, or similar, ligands can be used to attach terminal phosphate groups to a metal surface (e.g., using derivatized thiolalkanes or phosphines). Alternatively, the metal particles may be immobilized on a surface. Upon exposure to alkaline phosphatase, the phosphate groups would be cleaved, thus changing the charge of the metal surface. This change can be sensed using an electrostatic balance or by testing conductivity of the solution. Thus, metal surfaces are useful platforms for many devices, where enzyme surface alterations can be sensed by optical changes (using reflectance, or other methods), mass changes (sensed by e.g., a quartz microbalance whose frequency shifts with mass); electrical changes (e.g., of conductivity), or other methods.

Metal ions are not believed to be substrates for enzymes. Although some enzymes require metals as part of their active site, the metals themselves are not used up, but instead form part of the catalytic site with the enzyme to effect other reactions. Most metal ions are cations and require reduction and electrons for conversion to metal (zero oxidation state). The inventor is not aware of a teaching that oxidoreductase, or any other, enzymes might be useful to catalyze such reactions. In fact upon further investigation of the properties of peroxidases such a reaction would seem unlikely. Horseradish peroxidase, contains as a cofactor ferriprotoporphyrin (a heme group). When bound to the enzyme, the iron is in the +3 state and linked to a hydroxyl group. This hydroxyl group can be displaced by other anions, including cyanide, azide, fluoride, and its substrate, hydrogen peroxide. The reaction sequence of horseradish peroxidase is proposed to be:

Enzyme-H$_2$O+H$_2$O$_2$→Enzyme-H$_2$O$_2$ (complex I)+H$_2$O      a)

Enzyme-H$_2$O$_2$+AH$_2$→complex II+AH.      b)

complex II+AH.→Enzyme-H$_2$O+A      c)

where AH$_2$ is the reduced substrate and A is the oxidized substrate. Note that the substrate goes through a free radical form in step b wherein the free radical is denoted by the dot: "AH.". As an example, peroxidases catalyze the following reaction:

hydroquinone (reduced form)+H$_2$O$_2$→quinone (oxidized form)+2H$_2$O

Typically, an organic substrate is oxidized, while hydrogen peroxide is reduced. This is contrary to usage for metal ion reduction since it is desired to reduce the metal ion, not oxidize it. Furthermore, hydroquinone can reduce some metal ions (depending on concentrations and place in the electrochemical series, which orders half-reactions by redox potential). However peroxidase would remove hydroquinone from solution, instead generating the oxidized form (quinone), which will not reduce metal ions. One would logically conclude that peroxidases were therefore not suitable for reduction of metal ions.

Contrary to the above conclusion, a surprising and unexpected discovery was made that under some circumstances, enzymes can accept metal ions themselves as a substrate and reduce those metal ions to metal. Further the enzymes can deposit the reduced metal. For example, if horseradish peroxidase is combined with silver ions (silver acetate was used originally), and an appropriate reducing agent is added, e.g., hydroquinone, no enzyme-mediated reduction of metal occurs. However, upon addition of hydrogen peroxide, the enzyme accepts silver ions as a substrate and reduces them to silver metal, resulting in a metallic deposit (a citrate buffer was used at pH 3.8). Therefore another aspect of the invention is enzymatic reduction of metal ions.

It was found that bovine serum albumin and other non-enzyme proteins, for example, IgG, collagen, actin and myosin, when substituted for peroxidase, do not serve to deposit metal. This further confirms that the inventive metal deposition is enzymatic in nature.

Further exploration of this phenomenon revealed that pretreatment of the enzyme with gold ions (e.g., from potassium tetrabromoaurate), or silver ions (e.g., from silver acetate), followed by optional washing (to remove the excess pretreatment metal ion solution), resulted in greatly enhanced rates of silver deposition when the developing mix was subsequently applied. As used herein the term "developing mix" is defined as the solution applied to the enzyme to obtain metal deposition. Typically the developing mix contains metal ions (e.g., silver acetate), a reducing agent (e.g., hydroquinone) and an oxidizing agent (e.g., hydrogen peroxide) in a controlled pH buffer (e.g., 0.1 M sodium citrate, pH 3.8). In the above enzymatic metal reduction the developing mix advantageously comprised silver acetate, hydroquinone, and hydrogen peroxide in a citrate buffer at a pH of about 3.8. One preferred developing mix consists of 2.5 mg/ml hydroquinone, 1 mg/ml silver acetate, and 0.06% hydrogen peroxide in 0.1 M citrate buffer, pH 3.8. The enzymatic metal reduction and deposition can be conveniently observed when the enzyme is immobilized, for example, either on nitrocellulose paper, or immunologically attached to a target antigen.

Although the exact mechanism of this aspect of the invention has not been completely elucidated, it may be that hydrogen peroxide is reduced by the enzyme, but some electrons become available to also reduce silver metal. The hydroquinone is oxidized. It appears that peroxidase or its cofactor may similarly bind the pretreatment metal ions. These bound pretreatment metal ions then either enhance or retard the enzymatic reduction of metal ions supplied in the developing mix. The binding of metal ions (e.g., gold or silver) before the developing mix is applied may explain the alteration in metal deposition rates seen when the developing mix is applied. Thus, another aspect of the present invention comprises alteration of enzyme specificity using a developing mix to allow the enzyme to accept metal ions. A further aspect of the invention is modulation of the rate of metal deposition by pretreatment of the enzyme.

As discussed above a wide range of silver or gold pretreatment concentrations, including about 0.2% silver acetate or about 0.01% potassium tetrabromoaurate, serve to greatly enhance metal deposition. Surprisingly, use of more dilute pretreatment concentrations, particularly including about 0.01% silver acetate is found to substantially inhibit the subsequent enzymatic deposition reaction. While inhibition of the enzymatic reaction was unexpected, it provides a method to retard the enzymatic deposition of metals. Thus, another aspect of the invention provides methods to both stimulate and retard the enzymatic deposition of metals, thereby allowing further control of the enzymatic metal deposition process.

According to present invention, any suitable silver ions, such as silver acetate, silver lactate and silver nitrate, can be used in the peroxidase catalyzed silver deposition reactions. The silver ions can be used in liquid form, or emulsion form. Compared with silver nitrate, lactate and acetate are less easily soluble in water and more affected by light.

Naturally there are variations of the inventive aspects. It has been found that some other metal ions may be enzymatically reduced, including solutions of mercurous chloride, cesium chloride, lead nitrate, nickel sulfate, copper sulfate, palladium acetate and potassium ferrocyanide. Potassium ferrocyanide was reduced by peroxidase with hydroquinone adjusted to pH 10.

Other enzymes are also active toward reducing metal ions from their salts. For example, with a pretreatment of potassium tetrabromoaurate, catalase was found to reduce silver ions to silver metal when hydroquinone and hydrogen peroxide were included in a sodium citrate buffer at pH 3.8. Additionally lactoperoxidase was found to be active with silver ions.

While hydroquinone is presently the best known reducing agent, other reducing agents are also believed to be useful in practicing the invention, including, for example, n-propyl gallate, 4-methylaminophenol sulfate, 1,4 phenylenediamine, o-phenylenediamine, chloroquinone, bromoquinone, 2-methoxyhydroquinone, hydrazine, metal, ascorbic acid, 1-phenyl-3-pyrazolidinone (phenidone aminophenol) and dithionite salts such as sodium dithionite. 1-phenyl-3-pyrazolidinone, sodium borohydride and boranes may work as a reducing agent without the need for $H_2O_2$.

Enzymes may be coupled one after another to produce the desired metal deposit. For example, glucose serves as a substrate for glucose oxidase, producing hydrogen peroxide. The hydrogen peroxide then serves as a substrate for peroxidase to deposit silver ions in the presence of hydroquinone, since hydrogen peroxide is used in that enzyme reaction.

The enzyme altered metal product may be soluble or dispersible in water. Naturally in other embodiments of the invention the altered metal products can be soluble in organic solvents. For example, aurothioglucose with hydroquinone and hydrogen peroxide, when exposed to horseradish peroxidase bound to nitrocellulose, turns an intense yellow at the location of the enzyme, if left undisturbed. However, rinsing or agitation easily disperses the color. This reaction may be coupled to an optical density reader or used in an ELISA format with a microtiter plate reader that will sense the newly formed colored product.

The inventive metal deposits, formed from particles or ions, may be further intensified using autometallography. As used herein "autometallography" is defined as a deposition of metal from metal ions in solution that specifically occurs on a nucleating metal surface. For example, it is known that if gold particles in the size range of about 1 to 50 nm are exposed to silver ions and a reducing agent, silver metal is deposited on the gold particles forming a composite particle. As more silver is deposited the composite particle increases in size. As the composite particles become larger, they become more visible and detectable.

Autometallography may be combined with the inventive enzymatic metal deposition. Once metal has been enzymatically deposited as a metal particle, the metal particle is subjected to an autometallographic solution. The autometallographic deposit forms a composite particle and amplifies the size of the enzymatically deposited metal particle so that the enzymatic metal deposits are more voluminous and hence easier to detect. The novel combination of enzymatic metal deposition in tandem with autometallography provides increased sensitivity and/or more rapid detection.

A further advantage of the use of enzymatic metal deposition in tandem with autometallography is that the autometallographic deposit may be a different metal from that of the enzymatically deposited particle. This permits overcoating of the original enzymatic metal deposit by one or more different autometallographically deposited metal layers. The autometallographic layer may also become the bulk of the composite particle if desired. It should be noted that the autometallographic coating or coatings, may confer new properties to the enzymatic metal deposit, such as altered oxidation rates, magnetic properties, optical properties and electrical properties. For example, if gold is autometallographically deposited over an enzymatic silver deposit, this would confer improved chemical resistance as gold is more noble and more resistant to oxidation than the core silver deposit. Autometallographically depositing copper over a enzymatic metal deposit would confer the conductive, and other, properties of copper to the metal particle.

A wide variety of methods can be used to detect and observe the novel enzymatic metal deposits. In fact, the use of an enzymatic metal deposit overcomes many of the limitations of conventional enzyme-created fluorescent or colored particles. Some of the methods useful for detecting and observing an enzymatic metal deposit include:

Visual observation using the unaided eye. The enzymatic deposition of silver or silver after pretreating with gold typically results in a black or brown color due to the presence of finely divided metal. The color is easily seen by the unaided eye, especially against a light colored background.

Visual observation using a microscope. For higher resolution or more sensitive detection, the metal deposit may be viewed under a microscope. The metal is very dense and opaque, and may in many circumstances be easily detected by this density using bright field illumination. This feature is particular useful in chromogenic in situ hybridization (CISH) assays for detecting a target site or molecule in a sample. Compared with fluorescence in situ hybridization (FISH), CISH is a technique that allows in situ hybridization methods to be performed and detected with a bright-field microscope, instead of a fluorescence microscope as required for FISH. While FISH requires a modern and expensive fluorescence microscopes equipped with high-quality 60× or 100× oil immersion objectives and multi-band-pass fluorescence filters which are not used in most routine diagnostic laboratories, CISH allows detection with standard light (bright-field) microscopes which are generally used in diagnostic laboratories. Also, with FISH, the fluorescence signals can fade within several weeks, and the hybridization results are typically recorded with an expensive CCD camera, while the results of CISH do not generally fade allowing the tissue samples to be archived and reviewed later. Therefore, analysis and recording of FISH data is expensive and time consuming. Most importantly, tissue section morphology is not optimal in FISH. Generally, histological detail is better appreciated with bright-field detection, which is possible with CISH detection. A further advantage of CISH is that large regions of tissue section can be scanned rapidly after CISH counterstaining since morphological detail is readily apparent using low power objectives (e.g. 10× and 20×), while FISH detection generally requires substantially higher magnification, thus reducing the field of view. Such features like efficient processing and convenient viewing allow high throughput, automatic screening of a large number of samples by using automated sample processing and detection devices, such as automated immunohistochemistry slide preparation and staining devices. A typical example of such automated devices is the Benchmark XT automated platform provided by Ventana Medical Systems, Tucson, Ariz. Details of Benchmark XT automated platform are described in the manufacturer's user manual, product description and alike, and in U.S. Pat. No. 6,296,809, which are herein incorporated by reference in their entirety.

Reflectance. Since metals reflect light, epi-illumination may be used either with or without a microscope. Additionally, metals repolarize light upon reflection, so crossed polarizers may be used to filter out reflections from non-metallic material, thus improving the signal-to-noise ratio.

Electron microscopy. Metals are clearly seen via electron microscopy due to their density in transmission electron microscopy. They also have high backscatter coefficients, and may be viewed with a backscatter detector on a scanning electron microscope. Metals also give off characteristic x-rays upon electron bombardment, so they may be detected by x-ray detectors, or electron energy loss spectrometers. Other methods include detection of the characteristic electron diffraction patterns of metals.

Polarographic, electrochemical, or electrical detection. Metals deposited on an electrode alter its properties. By probing with the proper currents and voltages, metal can be detected.

X-ray spectroscopy. Metals can be detected by x-ray induced fluorescence or x-ray absorption.

Chemical tests. Sensitive tests exist for chemically converting metals into products that are colored or otherwise detectable.

Mass detection. The mass of the deposited metal is detected using, for example, a quartz crystal mass balance. A quartz crystal in an inductance-resistance-capacitance (LRC) electronic circuit with an alternating voltage supply oscillates at some resonant frequency. If metal is deposited on the surface of the quartz crystal, this changes the mass of the crystal and its resonant frequency. This provides a very sensitive method for measuring mass changes.

Light scattering. Fine metal deposits will alter the light scattering of a solution or surface.

Other optical methods of detecting interaction of metals with light, including absorption, polarization and fluorescence.

Magnetic detection. The magnetic properties of the deposited metal can be detected using appropriate equipment such as magnets, coils, or sensing optical-magnetic property changes.

Autometallography. Further amplification of the signal may be achieved by applying additional metal ions and reducing agent and other additives to effect further metal deposition that specifically nucleates on the initial enzymatic metal deposit.

Scanning probe microscopy. Metal deposits may be recognized at high spatial resolution and sensitivity by the various scanning probe microscope techniques, including scanning tunneling microscopy (STM), atomic force microscopy (AFM), near field optical microscopy (NSOM) and other related techniques using piezoelectrically driven scanned tips.

Many of the enzymes useful in the present invention are purified from living cells. Bacteria and living organisms have functioning enzymes. Thus another aspect of the invention is enzymatic metal deposition, under appropriate conditions, in vivo. As one example, an initial developing mix comprising 1 mg/ml silver acetate, 2.5 mg/ml hydroquinone and 0.06% hydrogen peroxide in 0.1 M citrate buffer, pH 3.8 was prepared. When the initial developing mix was diluted 1 part developing mix:1 part solution of a mixture of growing bacteria from pond water, the bacteria stained with silver metal deposits, but rapidly died.

As another example when the initial developing mix was diluted by adding 1 part of the above developing mix to 5 parts bacterial solution, the bacteria became black with internal silver deposits in a few minutes, but remained alive.

As a further example when the initial developing mix was diluted by adding 1 part of the above developing mix to 50 parts bacterial solution, the bacteria also became black with internal silver deposits, but over a longer period of about twenty four hours, and survived with no apparent toxicity. In each of the above examples the bacteria were intensely stained, much more so than with standard bacterial stains, and easily seen under a bright field light microscope. The use of enzymatic metal deposition in vivo provides a novel method of imaging and detecting bacteria and other live-cells.

These reagents for carrying out the inventive enzymatic metal deposition can be assembled into kits. As used herein, a "kit" refers to any delivery system for delivering materials or reagents for carrying out a method of the invention. In the context of reaction assays, such delivery systems include systems that allow for the storage, transport, or delivery of reaction reagents (e.g., oxidizing agents, reducing agents, metal ion solutions, probes, enzymes, etc. in the appropriate containers) and/or supporting materials (e.g., buffers, written instructions for performing the assay and trouble shooting, etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

The inventive enzymatic metal deposits are useful in a number of applications. Thus another aspect of the invention is the use of enzymatic metal deposits in such applications, including:

Immunohistochemistry and Immunocytochemistry:

Currently, antibodies are widely used to target antigens on cytologic specimens, tissue slices, and biopsies. The antibodies are then commonly detected by a variety of techniques including use of a secondary antibody that is biotinylated, followed by avidin-biotin-peroxidase complex (ABC complex), and development of a color with 3,3'-diaminobenzidine (DAB). Other detection methods include fluorescence and chemiluminescence. The present invention may be used as a detection scheme by supplying metal ions and a developing mix, preferably with a metal ion pretreatment, to the peroxidase localized to the antigen by the above described or analogous methods. Instead of depositing DAB, a metal, for example silver will be deposited. Enzymatic silver deposition has the advantage of better detectability not only by bright field microscopy (where a black deposit is formed), but also by reflectance microscopy, electron microscopy and other methods suited to metal detection. Sensitivity is therefore greatly improved over conventional methods.

Alternatively, the inventive metal clusters or colloids with surface enzyme substrates described above may be used to form antigen-specific deposits by enzymatic action. The enzymatic deposition of metals has a great advantage over simple targeting of metal nanoparticles attached to antibodies, as is commonly done using gold-antibody conjugates for electron microscopy, lateral flow tests, and other applications. One major advantage is that the metal or metal particles are continuously deposited by the enzyme, as long as more substrate is provided. In this way, huge amounts of metal product may be deposited compared to non-enzymatic targeting of metal particles, achieving a desirable amplification effect.

Thus, the popular DAB method used widely in pathology may be easily adapted to the more sensitive enzymatic metal deposition method described herein to easily achieve better results while requiring few changes and little additional expense.

In Situ Hybridization

Presently considerable laboratory and pathological testing is being done and it is desirable to have a sensitive method to detect DNA or RNA sequences in segments or in a genome. By hybridizing a complementary probe carrying a detectable moiety, these sequences can be found and quantified. However the limits of detection required to see single gene copies or low levels of expression exceed the capability of many methods. The present invention may be used to achieve sensitive detection of a target locus in a chromosome, single copies or low-level amplification of a target gene in a sample by having the nucleic acid probe labeled with an enzyme, for example peroxidase, or to use multistep labeling, such as a biotinylated probe, followed by avidin-biotin-peroxidase complex or biotin-antibody-peroxidase complex. The peroxidase is then utilized as previously described to deposit metals. The enzymatically deposited metals are highly detectable and as further described below single gene sensitivity has been achieved using this novel method.

Lateral Flow, Blots, and Membrane Probing

A number of useful applications, such as lateral flow diagnostics (e.g., the "dipstick" pregnancy test kit), Western, Southern, and other blots, and other tests performed on membranes, are presently in use. Currently, these methods employ radioactive, fluorescent, colloidal gold, chemiluminescent, colorimetric, and other detection schemes, each having the previously discussed drawbacks and limitations. The inventive enzymatic metal deposition method is readily used with the above applications. For example, the target can be probed with a binding moiety that carries an enzyme, for example peroxidase. The binding moieties useful depend on the desired target and include, for example, antibody, antibody fragments, antigen, peptide, nucleic acids, nucleic acid probes, carbohydrates, drugs, steroids, natural products from plants and bacteria and synthetic molecules that have an affinity for binding particular targets. Enzymatic metal deposition is then applied, using either metal particles with substrate shells or metal ions and an appropriate developing mix, to deposit metal in the vicinity of the specific target site. The metal deposit may be in the form of an attached deposit or dispersed in solution. The enzymatically deposited metals are highly detectable and provide an extremely sensitive detection method.

Sensitive Detection of Antigens and Other Materials

Many other formats for detection of antigens and other materials have been devised, such as use of gels, microtiter plate systems and surface sensors. Most of these may easily be adapted to accommodate the present invention and substitute enzymatic deposition of metals and subsequent detection in place of conventional techniques. This would transform the conventional formats into new and improved formats having desirable characteristics such as higher sensitivity, lower cost, permanency of record and other advantages. Substitution of enzymatic deposition of metals and subsequent detection in place of conventional techniques also eliminates many of the disadvantages of conventional systems, such as use of radioactive materials, bleaching, transitory products and high expense.

Electron Microscope Probes

Small amounts of metals are easily detected in electron microscopes by their density, backscatter, x-ray emission or energy loss. The invention herein can be used to specifically target antigens or other sites, initially with an enzyme followed by deposition of metal. The enzymatically deposited detectable metal allows the targeted sites to be analyzed with high specificity and sensitivity.

Nanotechnology and Nanofabrication

Since the present invention provides for deposition of metals at enzyme locations, unique materials and objects may be created. For example, a structure such as the regular arrays of muscle tissue may be treated with antibodies to the Z band. Then a secondary antibody conjugated to peroxidase is added to the muscle tissue. Finally, the enzyme is given a silver or gold pretreatment, followed by the enzymatic metal deposition. The Z bands are then converted to metal deposits creating a nanostructure of finely spaced metallic bands that would be difficult to fabricate by other means. The creation of many other objects and patterned objects ultimately containing metal using the present invention can be imagined by those skilled in the art and all such embodiments are encompassed by this invention. It should be noted that enzymatic deposition of magnetic metals will be useful in computer technology and data storage.

Biosensors

The present invention can be applied to provide a range of novel biosensors. Several modes of construction are possible, including amperometric, potentiometric, and optical. For example, an analyte will undergo an enzyme reaction as a substrate. The enzyme reaction may produce directly, or be coupled to another enzyme reaction to produce, a reducing agent or hydrogen peroxide. As a more specific example glucose oxidase oxidizes glucose to gluconic acid and hydrogen peroxide. Thus the enzyme reaction provides the hydrogen peroxide required for the reduction of a metal by peroxidase. The reduced metal is deposited on an electrode, altering the electrode current. The deposited metal can also be sensed polarographically by an alternating current. Potentiometric detection can be used by sensing the change in metal ion concentrations resulting from enzyme deposition. Optical biosensors can be made based on the large light absorption and scattering changes provided by enzymatic metal deposition.

Remediation

Mercury, lead and other toxic metals may be altered by the novel enzyme action described herein to convert toxic metal ions into insoluble metal, thus fixing the toxic substances and preventing the toxic ions from leeching into groundwater tables. The novel enzymatic action is useful to remove toxic metals from any water stream, such as manufacturing or water treatment plants.

Bacteria and Live Cell Staining

The instant invention has been used to intensely stain live bacteria, to a much higher degree than achievable using conventional bacterial stains. This has important implications for detection of bacteria in water, foods, and samples from patients. Simple metal detectors based on, for example, light scattering are made possible by the inventive enzyme metal deposit. Because the enzymatic metal deposit can be detected with high sensitivity, little or no culturing need be done. The elimination of the hours or days needed to grow pathogens to a detectable level so that they may be screened for antibiotic sensitivity solves a problem inherent with current technology. Naturally other live cells and organisms may similarly be stained with novel metal depositions using enzymes endogenous to that cell or organism.

Examples of Target Molecules Ill Biological Samples

The present invention can be applied to detection of a wide variety of biological molecules for research, genetic profiling, diagnosis, prevention and/or treatment of diseases and conditions. For example, the inventive method can be used to determine a disease status of a mammal, preferably a human subject, by detecting the level of the biomarker in a sample derived from the mammal. Such "disease status" may relate to disease determination or classification, prognosis, drug efficacy, patient responsiveness to therapy (the so-called "targeted therapy"), whether adjuvant or combination therapy is recommended, likelihood of recurrence of disease, or the like. For example, information on changes in levels of biomarkers in patients in response to drugs in clinical trials or treatment can be utilized to stratify patients into sub-populations that are more or less responsive to a particular drug, or susceptible to adverse side effects of the drug; a higher amount of the target biomarker in a patient sample in comparison with a reference sample of normal cells may indicate that the patient has a disease associated with aberrant amplification and/or expression of the biomarker.

Accordingly, the present invention provides a method for detecting a target molecule such as a biomarker in a test sample, comprising: binding an enzyme to the target molecule in the test sample; combining an enzyme with metal ions, an oxidizing agent and a reducing agent; incubating the enzyme with the metal ions in the presence of the oxidizing agent and the reducing agent, whereby the metal ions are reduced to elemental metal; depositing the elemental metal in the vicinity of the enzyme; and determining the presence of the deposited metal in the vicinity of the enzyme. The presence, amounts or levels of the deposited metal may be compared with those of a reference sample so as to determine the difference in the profile of the target molecule in the test sample and the reference sample. Such information can be used to determine the disease status of the patient from whom the test sample is derived.

As used herein, the reference samples typically have one or more cell, xenograft, or tissue samples that are representative of a normal or non-diseased state to which measurements on patient samples are compared to determine whether a biomarker is present in excess or is present in reduced amount in the patient sample. The nature of the reference sample is a matter of design choice for a particular assay and may be derived or determined from normal tissue of the patient himself or herself, or from tissues from a population of healthy individuals. Preferably, values relating to amounts of the biomarker in reference samples are obtained under essentially identical experimental conditions as corresponding values for patient samples being tested. Reference samples may be from the same kind of tissue as that the patient sample, or it may be from different tissue types, and the population from which reference samples are obtained may be selected for characteristics that match those of the patient, such as age, sex, race, and the like. In application of the invention, amounts of the biomarker on patient samples are compared to corresponding values of reference samples that have been previously tabulated and are provided as measured values, average ranges, average values with standard deviations, or like representations.

In one aspect, the method provided in the present invention can be used to detect receptors for angiogenic growth factors which belong to the family of the receptor tyrosine kinase and are intimately involved in tumor development and metastasis. Examples of such angiogenic growth factor receptors include, but are not limited to, receptor for fibrin (VE-cadherin), receptors for VEGF (Flt1 and KDR), receptor for VEGF-C and VEGF-D (Flt4), receptor for VEGF-165 (NP-1 and NP-2), receptors for angiopoeitin-1, -2, -3, and -4 (Tie 1 and Tie 2), receptors for FGF (FGF-R1, -R2, -R3 and -R4), receptor for PDGF (PDGF-R), receptor for ephrine A1-5 (Eph A1-8), and receptor for ephrine B1-5 (Eph B1-8). Sensitive detection of such receptors allows early diagnosis, prognosis, or staging of tumors, benign, malignant, or metastatic, and other conditions associated abnormal angiogenesis or neuvascularization.

The target molecules suitable for detection using the inventive method also include G protein coupled receptors (GPCR) such as receptor for sphingosie-1-phosphate or SPP and for lysophosphatidic acid or LSA (edg receptor), cytokine receptors such as receptor for tumor necrosis factor-$\alpha$ or TNF-$\alpha$ (TNF-$\alpha$ receptor) and receptor for interleukin-8 or IL-8 (IL-8 receptor), protease receptors such as receptor for urokinase (urokinase receptor), and integrins such as receptor for thromospondin-1 and -2 ($\alpha v\beta 3$ integrin and $\alpha 2v\beta 1$ integrin) and receptor for fibronectin ($\alpha v\beta 3$ integrin), and matrix metalloprotease. Also included are receptors for protein factors that have anti-angiogenic effects, such as receptor for angiostatin (angiostatin-R, also called Annexin II), receptor for angiostadin (angiostadin binding protein I), low-affinity receptors for glypicans, receptor for endostatin (endostatin-R), the receptor for endothelin-1 (endothelin-A receptor), receptor for angiocidin (angiocidin-R), the receptor angiogenin (angiogenin-R), receptors for thromospondin-1 and thromospondin-2 (CD36 and CD47), and the receptor for tumstatin (tumstatin-R).

In another aspect, the present invention can be applied to detect a kinase gene or product thereof for diagnostic or therapeutic purposes. For example, the level of the gene or its product can be detected to aid in the assessment of patients who have diseases associated with abnormal activity of the kinase and could benefit from a therapy using an inhibitor of the kinase.

In one variation, the kinase is a serine/threonine kinase such as a Raf kinase; and the kinase inhibitor is BAY 43-9006.

In another variation, the kinase is a protein kinase kinase such as Raf-mitogen-activated protein kinase kinase (MEK) and protein kinase B (Akt) kinase.

In yet another variation, the kinase is an extracellular signal-regulated kinase (ERK). Examples of the inhibitor of ERK include but are not limited to PD98059, PD184352, and U0126.

In yet another variation, the kinase is a phosphatidylinositol 3'-kinase (PI3K). Examples of the inhibitor of PI3K include but are not limited to LY294002.

Examples of the receptor tyrosine kinase include, but are not limited to, epidermal growth factor receptor family (EGFR), platelet-derived growth factor receptor (PDGFR) family, vascular endothelial growth factor receptor (VEGFR) family, nerve growth factor receptor (NGFR) family, fibroblast growth factor receptor family (FGFR) insulin receptor family, ephrin receptor family, Met family, and Ror family.

Examples of the epidermal growth factor receptor family include, but are not limited to, HER1, HER2/neu (or HER2/neu), HER3, and HER4.

Examples of the inhibitors of epidermal growth factor receptor family include, but are not limited to, trastruzumab (HERCEPTIN®); ZD1839 (IRESSA®), PD168393, CI1033, IMC-C225, EKB-569, and inhibitors binding covalently to Cys residues of the receptor tyrosine kinase.

In particular, the transmembrane tyrosine kinase receptor HER2/neu was identified as an oncogene overexpressed by about 30% of breast cancers. These HER2/neu-overexpressing breast cancers define a subset of breast tumors that are characteristically more aggressive, and women who develop them have a shorter survival. Trastuzumab, a humanized monoclonal antibody specific for HER2/neu, has been widely used in the management of metastatic HER2/neu-overexpressing breast cancers. As a single agent, it produces response rates similar to those of many single-agent chemotherapeutic agents active in metastatic breast cancer and has limited toxicity. Combining trastuzumab with chemotherapy can result in synergistic antitumor activity. Thus, the method of the present invention can be used to detect the HER2 gene or its product to guide the selection of the patients who may be more responsive to therapeutic invention targeting HER2, such as a therapy of trastuzumab. For example, the present invention can be applied to detect HER2 gene amplification by using a nucleotide probe specific to HER2 gene in formalin-fixed, paraffin-embedded breast cancer tissue samples as an aid in the assessment of breast cancer patients for whom treatment with trastuzumab is considered.

Examples of the vascular endothelial growth factor receptor family include, but are not limited to, VEGFR1, VEGFR2, and VEGFR3. An example of the inhibitor of the vascular endothelial growth factor receptor family includes, but is not limited to, SU6668.

Examples of the nerve growth factor receptor family include, but are not limited to, trk, trkB and trkC. Examples of the inhibitors of the nerve growth factor receptor family include, but are not limited to, CEP-701, CEP-751, and indocarbazole compound. Examples of the diseases associated with abnormal activity of the nerve growth factor receptor family include, but are not limited to, prostate, colon, papillary and thyroid cancers, neuromas and osteoblastomas.

Examples of the Met family include, but are not limited to, Met, TPR-Met, Ron, c-Sea and v-Sea. Examples of disease associated with activity of the receptor tyrosine kinase from Met family include, but are not limited to, invasively ingrowing tumor, carcinoma, papillary carcinoma of thyroid gland, colon, carcinoma, renal carcinoma, pancreatic carcinoma, ovarian carcinoma, head and neck squamous carcinoma.

Examples of the non-receptor tyrosine kinase include, but are not limited to, the Kit family (e.g., c-Kit), Src family, Fes family, JAK family, Fak family, Btk family, Syk/ZAP-70 family, and Abl family.

In particular, the Kit receptor tyrosine kinase is a transmembrane receptor that is expressed in a variety of different tissues and mediates pleiotropic biological effects through its ligand stem cell factor (SCF). Sporadic mutations of Kit as well as autocrine/paracrine activation mechanisms of the SCF/Kit pathway have been implicated in a variety of malignancies, where its primary contribution to metastases is in enhancing tumor growth and reducing apoptosis. For example, Kit is frequently mutated and activated in gastrointestinal stromal tumors (GISTs) and there is ligand-mediated activation of Kit in some lung cancers. Kit is a convenient target in Kit-induced tumors and inhibition of this receptor with the small molecule drug Gleevec® (imatinib mesylate, STI571) in GIST has shown dramatic efficacy. Thus, the method of the present invention can be used to detect the Kit gene or its product to guide the selection of the patients who may be more responsive to therapeutic invention targeting Kit, such as a therapy of imatinib mesylate. For example, the present invention can be applied to detect c-Kit protein by using a primary antibody specific to c-Kit (anti-c-Kit antibody) in formalin-fixed, paraffin-embedded GIST tissue samples as an aid in the diagnosis of GIST in the context of the patient's clinical history, tumor morphology, and other diagnostic tests evaluated by a qualified pathologist.

Examples of the non-receptor tyrosine kinases from the Src family include, but are not limited to, Src, c-Src, v-Src, Yes, c-Yes, v-Yes, Fyn, Lyn, Lck, Blk, Hck, Fgr, c-Fgr, v-Fgr, p56lck, Tkl, Csk, and Ctk.

Examples of the inhibitors of the non-receptor tyrosine kinase from the Src family include, but are not limited to, SU101 and CGP 57418B.

Examples of the diseases associated with activity of the non-receptor tyrosine kinase from the Src family include, but are not limited to, breast cancer, carcinoma, myeloma, leukemia, and neuroblastoma.

Examples of the non-receptor tyrosine kinases from the Fes family include, but are not limited to, c-fes/fps, v-fps/fes, p94-c-fes-related protein, and Fer.

Examples of the diseases associated with activity of the non-receptor tyrosine kinase from the Fes family include, but are not limited to, tumor of mesenchymal origin and tumor of hematopoietic origin.

Examples of the non-receptor tyrosine kinases from the JAK family include, but are not limited to, Jak1, Jak2, Tyk2, and Jak3.

Examples of the inhibitors of the non-receptor tyrosine kinase from the JAK family include, but are not limited to, tyrphostin, member of CIS/SOCS/Jab family, synthetic component AG490, dimethoxyquinazoline compound, 4-(phenyl)-amino-6,7-dimethoxyquinazoline, 4-(4'-hydroxyphenyl)-amino-6,7-dimethoxyquinazoline, 4-(3'-bromo-4'-hydroxylphenyl)-amino-6,7-dimethoxyquinazoline, and 4-(3',5'-dibromo-4'-hydroxylphenyl)-amino-6,7-dimethoxyquinazoline.

Examples of the diseases associated with activity of the non-receptor tyrosine kinase from JAK family include, but are not limited to, tumor of mesenchymal origin and tumor of hematopoietic origin.

Examples of the non-receptor tyrosine kinases from the Fak family include, but are not limited to, Fak and CAKβ/Pyk2/RAFTK.

Examples of the inhibitors of the non-receptor tyrosine kinases from the Fak family include, but are not limited to, a dominant negative mutant S1034-FRNK; a metabolite FTY720 from Isaria sinclarii, and FAK antisense oligonucleotide ISIS 15421.

Examples of the diseases associated with abnormal activity of the non-receptor tyrosine kinases from Fak family include, but are not limited to, human carcinoma, metastasis-prone tumor, and tumor of hematopoietic origin.

Examples of the non-receptor tyrosine kinase from the Btk family include, but are not limited to, Btk/Atk, Itk/Emt/Tsk, Bmx/Etk, and Itk, Tec, Bmx, and Rlk.

Examples of the inhibitors of the non-receptor tyrosine kinases from Btk family include, but are not limited to, alpha-cyano-beta-hydroxy-beta-methyl-N-(2,5-dibromophenyl) propenamide.

Examples of the diseases associated with abnormal activity of the non-receptor tyrosine kinase from the Btk family include, but are not limited to, B-lineage leukemia and lymphoma.

Examples of the non-receptor tyrosine kinases from the Syk/ZAP-70 family include, but are not limited to, Syk and ZAP-70.

Examples of the inhibitors of the non-receptor tyrosine kinases from the Syk/ZAP-70 family include, but are not limited to, piceatannol, 3,4-dimethyl-10-(3-aminopropyl)-9-acridone oxalate, and acridone-related compound.

Examples of the diseases associated with abnormal activity of the non-receptor tyrosine kinases from the Syk/ZAP-70 family include, but are not limited to, benign breast cancer, breast cancer, and tumor of mesenchymal origin.

In yet another aspect, the present invention can be applied to detect the gene or gene product of a nuclear hormone receptor, such as estrogen, androgen, retinoid, vitamin D, glucoccoticoid and progesterone receptors. Nuclear hormone receptor proteins form a class of ligand activated proteins that, when bound to specific sequences of DNA serve as on-off switches for transcription within the cell nucleus. These switches control the development and differentiation of skin, bone and behavioral centers in the brain, as well as the continual regulation of reproductive tissues. Interactions between nuclear hormone receptors and their cognate ligands have been implicated in the initiation and development of various forms of cancer such as breast, prostate, bone, and ovarian cancer. Thus, by detecting the genes or gene products of the nuclear hormone receptors, diagnosis, prognosis and/or treatment of these diseases can be achieved.

Other than the specified diseases or conditions associated with the biomarkers described above, the present invention can also be used to detect the biomarkers in research, diagnosis, prognosis and/or treatment of diseases or disorders associated with undesirable, abnormal cell growth. Such diseases or disorders include, but are not limited to, restenosis (e.g. coronary, carotid, and cerebral lesions), benign tumors, a various types of cancers such as primary tumors and tumor metastasis, hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Examples of benign tumors include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

Specific types of cancers include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell tumor, primary brain tumor, acute and chronic lymphocytic arid granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyoma tumor, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, medulloblastoma, leukemias, lymphomas, malignant melanomas, epidermoid carcinomas, and other carcinomas and sarcomas.

Examples of diseases associated with abnormal angiogenesis include, but are not limited to, rheumatoid arthritis, ischemic-reperfusion related brain edema and injury, cortical ischemia, ovarian hyperplasia and hypervascularity, (polycystic ovary syndrome); endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy.

Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasias, syphilis, Mycobacteria infections, lipid degeneration, chemical burns, bacterial ulcers, fungal ulcers, Herpes simplex infections, Herpes zoster infections, protozoan infections and Kaposi sarcoma.

The present invention can also be applied to detect variation in nucleic acid sequences. The ability to detect variations in nucleic acid sequences is of great importance in the field of medical genetics: the detection of genetic variation is essential, inter alia, for identifying polymorphisms for genetic studies, to determine the molecular basis of inherited diseases, to provide carrier and prenatal diagnosis for genetic counseling and to facilitate individualized medicine. Detection and analysis of genetic variation at the DNA level has been performed by karyotyping, analysis of restriction fragment length polymorphisms (RFLPs) or variable nucleotide type polymorphisms (VNTRs), and more recently, analysis of single nucleotide polymorphisms (SNPs). See e.g. Lai E, et al., Genomics, 1998, 15; 54(1):31-8; Gu Z, et al., Hum Mutat. 1998; 12(4):221-5; Taillon-Miller P, et al., Genome Res.

1998; 8(7):748-54; Weiss K M., Genome Res. 1998; 8(7): 691-7; Zhao L P, et al., Am J Hum Genet. 1998; 63(1):225-40.

According to the present invention, for example, a nucleic acid probe for a SNP can be labeled with an enzyme, e.g., peroxidase, covalently or non-covalently, and hybridize to the site of the SNP. The enzyme is then utilized as previously described to deposit metal at the site of the SNP specifically. Multiple probes can be utilized for detecting multiple SNPs in a population of target polynucleotides in parallel as well by following the general principles described herein.

Having generally described certain aspects of the invention, the following examples are included for purposes of illustration so that the invention may be more readily understood and are in no way intended to limit the scope of the invention unless otherwise specifically indicated.

EXAMPLES

Example 1

Enzymatic Deposition of Silver Metal

One microgram of horseradish peroxidase was applied to a nitrocellulose membrane and allowed to dry. The membrane was then optionally blocked using 4% bovine serum albumin and washed. A solution containing 2.5 mg/ml hydroquinone and 1 mg/ml silver acetate in a 0.1 M citrate buffer, pH 3.8 was applied. Next, hydrogen peroxide was added and mixed to a final concentration of 0.03 to 0.06%. Silver deposition selectively occurred at the peroxidase spot as evidenced by a black product. No deposit occurred if the hydrogen peroxide was omitted.

Example 2

Enhanced Enzymatic Deposition of Silver Metal; Pretreatment with Silver Ions

One microgram of horseradish peroxidase was applied to a nitrocellulose membrane and allowed to dry. The membrane was then optionally blocked using 4% bovine serum albumin and washed. A solution of 2 mg/ml silver acetate in water was applied for three to five minutes, then washed with water. A solution containing 2.5 mg/ml hydroquinone and 1 mg/ml silver acetate in a 0.1 M citrate buffer, pH 3.8 was applied. Next, hydrogen peroxide was added and mixed to a final concentration of 0.03 to 0.06%. Silver deposition immediately and selectively occurred at the peroxidase spot as evidenced by an intense black product. No silver deposit occurred if the hydrogen peroxide was omitted.

Example 3

Enhanced Enzymatic Deposition of Silver Metal; Pretreatment with Gold Ions

One microgram of horseradish peroxidase was applied to a nitrocellulose membrane and allowed to dry. The membrane was then optionally blocked using 4% bovine serum albumin and washed. A solution of 0.1 mg/ml potassium tetrabromoaurate in water was applied for five minutes, then briefly washed with water. A solution containing 2.5 mg/ml hydroquinone and 1 mg/ml silver acetate in a 0.1 M citrate buffer, pH 3.8 was applied. Next, hydrogen peroxide was added and mixed to a final concentration of 0.03 to 0.06%. Silver deposition immediately and selectively occurred at the peroxidase spot as evidenced by an intense brown-black product.

Example 4

Enzymatic Deposition of Gold Nanoparticles

Gold nanoparticles having a diameter in the range of about 1-3 nm and a nominal diameter of 1.4 nm were prepared and ligand stabilized with 4-hydroxythiophenol and a glutathione such that the 4-hydroxythiophenol was 30% of the ligand mixture. The gold particles were purified on an Amicon GH25 gel filtration column to remove unreacted materials. One microgram of horseradish peroxidase was applied to a nitrocellulose membrane and allowed to dry. The membrane was then optionally blocked using 4% bovine serum albumin and washed. A $10-6$ M solution of the functionalized gold nanoparticles in 50 mM Tris buffer, pH 7.6 was applied. Next, hydrogen peroxide was added and mixed to a final concentration of 0.03 to 0.06%. A brown spot appeared at the peroxidase.

Example 5

Sensitive Immunological Detection of Antigen Using Enzymatic Metal Deposition

Figure 4:
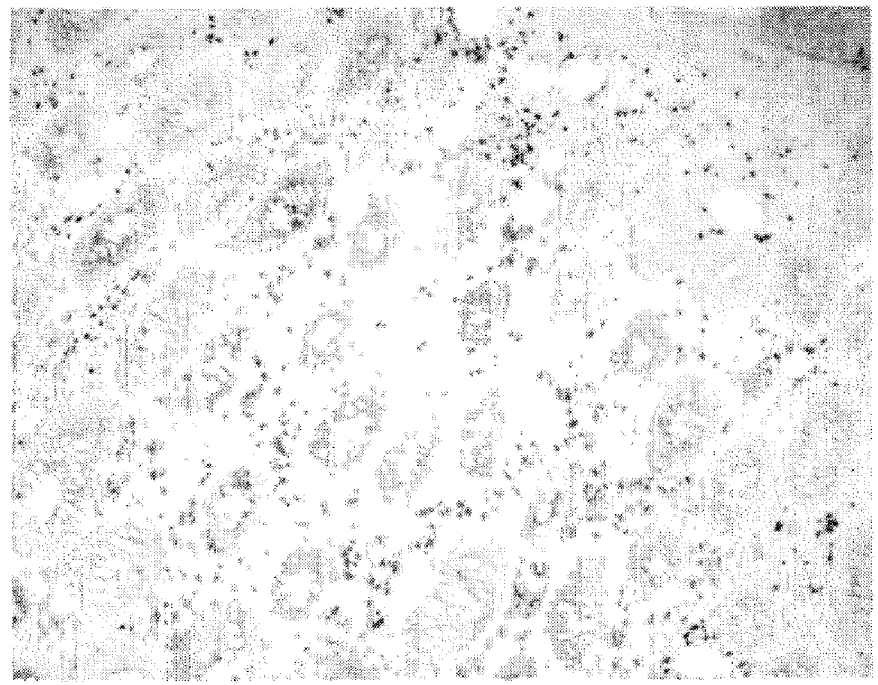
FIG. 4 illustrates the results of an immunostaining test incorporating an aspect of the invention using an antibody, peroxidase, and enzyme metal deposition. Similarly to the procedure used in FIG. 3, human colon carcinoma tissue was fixed in formalin and embedded in paraffin. Next it was sectioned and placed on glass slides for the light microscopy. Sections were deparaffinized with toluene, and rehydrated through successive washes in 100%, 95%, 80%, 70% ethanol, and finally phosphate buffered saline (PBS: 0.01M sodium phosphate, 0.14M sodium chloride, pH 7.4). Endogenous peroxide was quenched by incubating with 2 drops of 3% hydrogen peroxide for 5 minutes, followed by washing in PBS. Sections were then incubated with a biotinylated monoclonal antibody to an antigen in the section for 1 hour at room temperature. After washing with PBS, the sections were next incubated with a streptavidin-peroxidase conjugate for 20 min. After washing with water, the sections were incubated with a solution of 2 mg/ml silver acetate in water for three minutes, then washed with water. A solution containing 2.5 mg/ml hydroquinone and 1 mg/ml silver acetate in a 0.1 M citrate buffer, pH 3.8 was applied, and 3% hydrogen peroxide was added and mixed to achieve a final hydrogen peroxide concentration of 0.06%. Slides were observed in the light microscope and metal deposition was stopped with a water wash after 15 min. Intense silver metal staining was observed at the expected locations. Compared to the conventional immunostaining using the AEC substrate shown in FIG. 3, the enzyme metal deposition shown here had a similar distribution to the AEC red product, but the metal deposition was more intense, of better resolution, and clearly more sensitive. Controls where the streptavidin-peroxidase was deleted from the procedure showed little background and were clearly negative. Full width of bright field light micrograph shown is 250 microns.

Human colon carcinoma resected material was fixed in formalin, paraffin embedded, sectioned, and placed on glass slides for light microscopy. Sections were deparaffinized with toluene, and rehydrated through successive washes in 100%, 95%; 80%, 70% ethanol, and finally phosphate buffered saline (PBS: 0.1M sodium phosphate, 0.14M sodium chloride; pH 7.4). Endogenous peroxide was quenched by incubating with 2 drops of 3% hydrogen peroxide for 5 minutes, followed by washing in PBS. Sections were then incubated with a biotinylated monoclonal antibody to an antigen in the section for 1 hour at room temperature. After washing with PBS, the sections were next incubated with a streptavidin-peroxidase conjugate for 20 min. After washing with water, the sections were incubated with a solution of 2 mg/ml silver acetate in water for three minutes, then washed with water. A solution containing 2.5 mg/ml hydroquinone and 1 mg/ml silver acetate in a 0.1 M citrate buffer, pH 3.8 was applied, and hydrogen peroxide was added and mixed to a final concentration of 0.06%. Slides were observed in the light microscope and metal deposition was stopped with a water wash after 15 min. As shown in FIG. 4, intense silver metal staining was observed at the antigenic positions detected using conventional means. Parallel slides done using aminoethyl carbinol as the peroxidase substrate showed a similar distribution of red product staining, but it was much less intense, of poorer resolution and clearly less sensitive than the metal deposition slides. See FIG. 3. Controls where the streptavidin-peroxidase was deleted from the procedure showed little background and were clearly negative.

Example 6

Detection of a Single Gene in a Single Cell Using Enzymatic Metal Deposition

Figure 5:
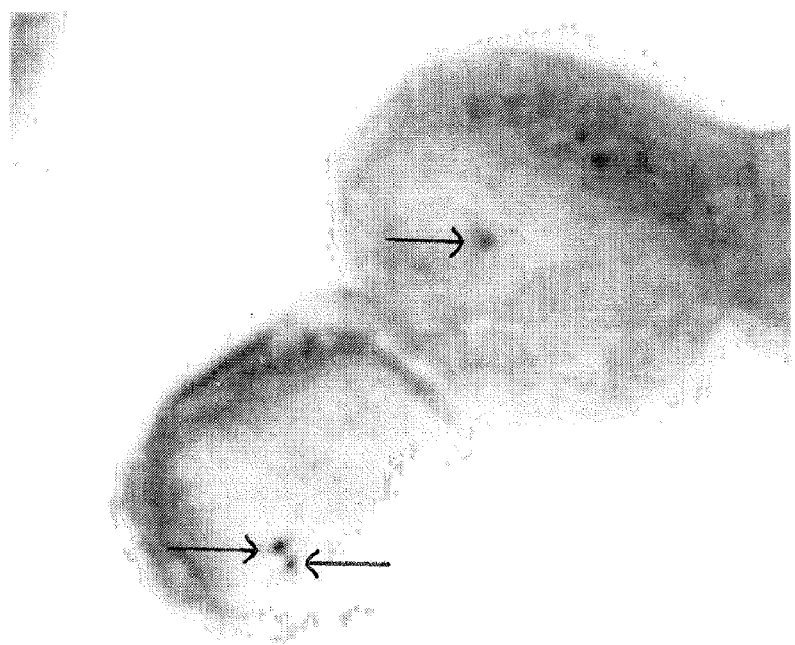
FIG. 5 illustrates the detection: of a single gene in a single cell using the inventive enzyme metal deposition. Silver deposits appear at the targeted gene site and are evident in the bright field light micrograph. This demonstrates the high sensitivity of enzyme metal deposition to detect single gene copies within individual cells. In the micrograph, the lower cell shows two dense black spots, indicated with arrows, close together, representing the gene on the pair of chromosomes, as expected, since cells have pairs of chromosomes. In the upper cell, two dense spots, indicated with arrows, are also seen in the cell; they are more widely separated since these cells are in interphase, and the chromosomes are randomly placed. Full width of bright field light micrograph is 20 microns.

With reference to FIG. 5, human breast cancer biopsies were fixed, embedded and sectioned. In situ hybridization was performed by standard procedures, such as removal of paraffin, treatment with proteinase K, and hybridization with a fluoresceinated probe for the HER2/neu gene. After hybridization, and washing, a biotinylated anti-fluorescein antibody was applied, followed by streptavidin conjugated to horseradish peroxidase. Then the sample was pretreated with a gold salt solution, and after washing was exposed to silver acetate, hydroquinone and hydrogen peroxide. Silver deposits appeared at the targeted gene site and were evident by bright field light microscopy. This demonstrated the high sensitivity of the enzyme metal deposition to detect single gene copies within individual cells.

More specifically, the formalin fixed, paraffin embedded and sectioned tissue was deparaffinized by treating with xylene 2×5 min. This was followed by 100% alcohol (2×1 min), 95% alcohol (2×1 min); a water soak (5 min), Dako-Target retrieval solution (40 min at 95° C., then 20 min cool down at room temperature (RT)), a water rinse (5 min with several changes), proteinase K (Dako 1:5000 in 50 mM Tris 5 min @ RT), a water rinse (1×1 min), 80% alcohol (1×1 min), 95% alcohol (1×1 min), 100% alcohol (1×1 min, allowing to air dry), probe addition (10 microliters of probe, coverslip added and sealed; stored overnight), codenaturation (6 min @ 90° C.), hybridization (37° C. overnight), coverslip soak (remove cement, 2×SSC buffer soak for 5 min), stringent wash (0.5×SSC, 72° C., 5 min), wash in dd (double distilled) water (2 min), Lugol's iodine (immerse slide for 5 min), dd water (3 rinses), 2.5% sodium thiosulfate (immerse slide for a few sec until tissue clears), dd water (3-5 rinses, 7 min total), 1XPBS (phosphate buffered saline)+0.1% Tween 20 (3 min RT), primary antibody incubation (Anti-fluorescein-biotin, 1:100 in PBS, pH 7.6 with 1% BSA (bovine serum albumin), 50 microliters, apply plastic coverslip, 30 min @ RT), 1XPBS+ 0.1% Tween 20 (3×5 min, RT), PBS, pH 7.6, 0.1% fish gelatin (immerse for 5 min), streptavidin-peroxidase (1:200, diluted with PBS pH 7.6 with 1% BSA, 50 microliters, plastic coverslip, 60 min @ RT), wash PBS pH 7.6 (2×5 min), PBS pH 7.6, 0.1% fish gelatin (immerse for 5 min), rinse in dd water (10 min several changes), 0.1 mg/ml potassium tetrabromoaurate in water (5 min), dd water (3×1 min), substrate silver ions and developing mix (2.5 mg/ml hydroquinone, 1 mg/ml silver acetate, 0.06% hydrogen peroxide in 0.1 M citrate buffer, pH 3.8; observe development), stop metal deposition with water wash (2×3 min), hematoxylin stain (1 min), water rinse, alcohol-xylene.

Example 7

Enzymatic Deposition of Gold Particles Having 3,3'-Diaminobenzidine Attached

Gold nanoparticles having a diameter in the range of about 1-3 nm were synthesized by reduction of potassium tetrabromaurate with sodium borohydride, including the thiol ligand glutathione and 3,3'-diaminobenzidine. The nanoparticles were then purified from starting materials by size exclusion column chromatography on an Amicon GH25 column with water as the eluent. Particles were then incubated with horseradish peroxidase immobilized on a nitrocellulose membrane, with addition of hydrogen peroxide to a final concentration of 0.03%. Gold particles were found to deposit selectively at the peroxidase location.

Example 8

Detection of Live Bacteria Using Enzymatic Metal Deposition

Figure 6:
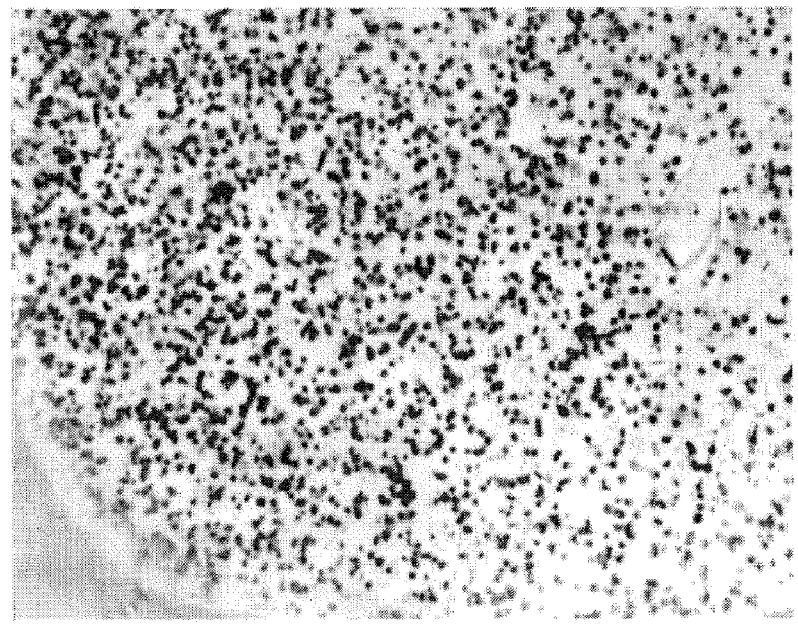
FIG. 6 illustrates detection of live bacteria using the inventive enzyme metal deposition. A sample of water microscopically revealed bacterial organisms under phase contrast light microscopy. 1000 parts of the water sample was incubated with 1 part of the developing mix (comprising 1 mg/ml silver acetate, 2.5 mg/ml hydroquinone and 0.06% hydrogen peroxide in 0.1 M citrate buffer, pH 3.8). The live bacteria became intensely stained black with silver deposits and were easily seen in bright field. The bacteria were actively moving, so were captured with a shutter speed of 0.08 sec under bright field conditions using an oil immersion lens at a magnification of 1000×. Most of the bacteria (black spots) were round, or cocci bacteria, but a few rodlike (bacilli) bacteria can be seen in the micrograph. All of the bacteria remained alive for more than a month. Full width of this micrograph is 100 microns.

A sample of pond water microscopically revealed bacterial organisms under phase contrast light microscopy. An aliquot was mixed, 1 part developing mix to 5 parts pond water. The developing mix consisted of 1 mg/ml silver acetate, 2.5 mg/ml hydroquinone and 0.06% hydrogen peroxide in 0.1M citrate buffer, pH 3.8. Over time the bacteria became dark, and after a few minutes the bacteria were visible by bright field microscopy (whereas they were not seen in this mode previously). The bacteria remained alive. In another case, 1000 parts tap water was incubated with 1 part of the developing mix. After several days, live bacteria were intensely stained black with silver deposits and were easily seen in bright field. See FIG. 6. The bacteria remained alive for more than a month.

Example 9

Enzymatic Deposition of Iron

One microgram of horseradish peroxidase was adsorbed to nitrocellulose, dried, then blocked with 4% bovine serum albumin. A solution containing 1% potassium ferrocyanide, 0.5% hydroquinone, and 0.06% hydrogen peroxide in a 0.1 M citrate buffer, pH 3.8 was incubated with the target enzyme. In a few minutes, a deposit of iron was visible as a dense spot at the peroxidase site.

Example 10

Enzymatic Deposition of Mercury

One microgram of horseradish peroxidase was adsorbed to nitrocellulose, dried, then blocked with 4% bovine serum albumin. A solution containing 0.5% mercurous chloride, 0.25% hydroquinone, and 0.06% hydrogen peroxide in a 0.1 M citrate buffer, pH 3.8 was incubated with the target enzyme. In a few minutes, a deposit of mercury was visible as a dense spot at the peroxidase site.

Example 11

Enzymatic Deposition of Nickel

One microgram of horseradish peroxidase was adsorbed to nitrocellulose, dried, then blocked with 4% bovine serum albumin. A solution containing 5% nickel sulfate, 0.25% hydroquinone, and 0.06% hydrogen peroxide in a 0.1 M citrate buffer, pH 3.8 was incubated with the target enzyme. In a few minutes, a deposit of nickel was visible as a dense spot at the peroxidase site.

Example 12

Enzymatic Deposition of Copper

One microgram of horseradish peroxidase was adsorbed to nitrocellulose, dried, then blocked with 4% bovine serum albumin. A solution containing 5% copper sulfate, 0.25% hydroquinone, and 0.06% hydrogen peroxide in a 0.1 M citrate buffer, pH 3.8 was incubated with the target enzyme. In a few minutes, a deposit of copper was visible as a dense spot evident at the peroxidase site.

Example 13

Lactoperoxidase Catalyzed Deposition of Silver

Several beads of immobilized lactoperoxidase were mixed with a solution containing 0.25% hydroquinone, 0.1% silver acetate, and 0.06% hydrogen peroxide in a 0.1 M citrate buffer, pH 3.8. Many of the beads turned black in color as a result of silver deposition.

Example 14

Enzymatic Deposition of Silver Using Catalase

One microgram of catalase was adsorbed to nitrocellulose, dried, then blocked with 4% bovine serum albumin. An aqueous solution containing 0.01% potassium tetrabromoaurate was preincubated with the enzyme, then washed. Next, a solution of 0.25% hydroquinone, 0.1% silver acetate, and 0.06% hydrogen peroxide in a 0.1 M citrate buffer, pH 3.8 was incubated with the target enzyme. In a few minutes, a deposit of silver was visible as a dense spot at the catalase site.

Example 15

Soluble Colored Compound Containing Gold Formed Upon Enzyme Action on Aurothioglucose One microgram of horseradish peroxidase was adsorbed to nitrocellulose, dried, then blocked with 4% bovine serum albumin. A solution containing 0.5% aurothioglucose was incubated with the enzyme in a solution also containing 0.25% hydroquinone and 0.06% hydrogen peroxide in a 0.1 M citrate buffer, pH 3.8. In a few minutes, an intense yellow colored gold product was evident at the peroxidase site. The gold product was soluble and could be easily redistributed in the solution if mixed.

Example 16

Enzymatic Deposition of Gold Particles Stabilized with Thioglucose

Gold nanoparticles having thioglucose bound to their surfaces were prepared. The particles were purified by gel filtration chromatography to remove any excess reactants. One microgram of horseradish peroxidase was adsorbed to nitrocellulose, dried, then blocked with 4% bovine serum albumin. A solution containing 0.5 O.D. at 420 nm of the gold particles was incubated with the enzyme in a solution also containing 0.25% hydroquinone and 0.06% hydrogen peroxide in a 0.1 M citrate buffer, pH 3.8. In a few minutes, an brown product was evident at the peroxidase site, indicating deposition of the nanoparticles.

Example 17

Sensitive Immunological Detection Using Enzymatic Metal Deposition

Human breast biopsy material was prepared in a manner similar to Example 5. Four tests were done on the biopsy material using the inventive enzymatic metal deposition and conventional (DAB) staining techniques:
  1. breast cancer, testing for and localizing the estrogen receptor (ER);
  2. breast cancer, testing for and localizing the progesterone receptor (PR);
  3. breast cancer, testing for and localizing the Her2-neu oncoprotein; and
  4. breast cancer, testing for and localizing the Her2-neu oncoprotein, Slides were observed in the light microscope and metal deposition was stopped with a water wash after 15 min. The samples prepared using the inventive enzymatic metal deposition method had deposits of much higher resolution than the conventionally stained test samples, so that, for example, membrane proteins were clearly localized to the membrane. The metal deposit signal was very intense and black with a higher density than the conventionally stained test samples. There was no background using the inventive method. Parallel slides done using DAB resulted in a brown signal that was less dense than the signal produced using the inventive method.

Example 18

Enzymatic Deposition of Metal Using 4-Methylaminophenol Sulfate as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 4-methylaminophenol sulfate (also called metol or elon) was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 19

Enzymatic Deposition of Metal Using 1,4 Phenylenediamine as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 1,4 phenylenediamine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 20

Enzymatic Deposition of Metal Using o-Phenylenediamine as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of o-phenylenediamine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 21

Enzymatic Deposition of Metal Using Chloroquinone as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of chloroquinone was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 22

Enzymatic Deposition of Metal Using Bromoquinone as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of bromoquinone was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 23

Enzymatic Deposition of Metal Using 2-Methoxy'Hydroquinone as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 2-methoxyhydroquinone was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 24

Enzymatic Deposition of Metal Using Hydrazine as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of hydrazine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 25

Enzymatic Deposition of Metal Using Dithionite Salt (e.g., Sodium Dithionite) as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of sodium dithionite was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 26

Enzymatic Deposition of Metal Using Thioglucose as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 100 mg/ml solution of thioglucose was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 27

Enzymatic Deposition of Metal Using Glucosamine as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 20 microliters of a 5 mg/ml solution of glucosamine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 28

Enzymatic Deposition of Metal Using Sodium Metabisulfite as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of sodium metabisulfite was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 29

Enzymatic Deposition of Metal Using Aminophenol as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of aminophenol was applied with mixing. An identical test was prepared except that additionally 3 microliters of a 3% hydrogen peroxide solution was added with mixing. The sample with the hydrogen peroxide showed specific deposition of silver metal at the horseradish peroxide site on the nitrocellulose, as evidenced by a dark metallic spot congruent with the position of the bound enzyme. A spot over the enzyme also developed in the sample without hydrogen peroxide, indicating that the hydrogen peroxide may not be required in this case.

Example 30

Enzymatic Deposition of Metal Using 1-Phenyl-3-Pyrazolidinone (Phenidone) as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 1-phenyl-3-pyrazolidinone 1 was applied with mixing. An identical test was prepared except that additionally 3 microliters of a 3% hydrogen peroxide solution was added with mixing. The sample with the hydrogen peroxide showed specific deposition of silver metal at the horseradish peroxide site on the nitrocellulose, as evidenced by a dark metallic spot congruent with the position of the bound enzyme. A spot over the enzyme also developed in the sample without hydrogen peroxide, indicating that the hydrogen peroxide may not be required in this case.

Example 31

Enzymatic Deposition of Metal Using Borohydride as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 8. Next, 5 microliters of a 1 mg/ml solution of sodium borohydride was applied with mixing. An identical test was prepared except that additionally 3 microliters of a 3% hydrogen peroxide solution was added with mixing. The sample with the hydrogen peroxide showed specific deposition of silver metal at the horseradish peroxide site on the nitrocellulose, as evidenced by a dark metallic spot congruent with the position of the bound enzyme. A spot over the enzyme also developed in the sample without hydrogen peroxide, indicating that the hydrogen peroxide may not be required in this case.

Example 32

Detection of Single Copy of HER2 Gene in Tissue

In this example, the method of the present invention was used to sensitively and selectively detect a single copy of a gene in situ, such as HER2 gene in normal as well as in breast cancer tissue.

Formalin-fixed, paraffin-embedded (FFPE) human breast carcinoma containing normal breast epithelium was used as a positive control. The slides containing the FFPE tissue were prepared and stained automatically by using an automated staining system BENCHMARK XT (Ventana Medical Systems, Inc., Tucson, Ariz.) operated in accordance with standard procedures.

The pre-programmed protocol "XT SISH iVIEW™ SILVER" was used to prepare and stain all tissues via automated in situ hybridization. The deparaffinization option was selected for 20 minutes at 75° C. under the EZ Prep™ solution. The solution is applied through the-rinse nozzles which leaves approximately 200-300 ul of residual volume of the solution on the slide. The slide is then incubated at temperature for 4 minutes. This process cycles 5 times. The cell conditioning option was also selected, and was performed under CC2 reagent (which is a high pH retrieval solution that serves to solubilize the cell membrane which allows genetic material to be accessible for target probe hybridization). The solution is applied into a residual volume of EZ prep and heated (Ventana Medical Systems Product No. 950-123) at 90° C. for 20 minutes. Following cell conditioning, protease digestion was selected using Protease III, a type VIII protease isolated from *Bacillus Licheniformus*. Approximately 100 ul of protease III is dispensed into 200-300 ul of reaction buffer and incubated for 4 minutes at 37° C. (Ventana Medical Systems Product No. 780-4149). The detection system applied to the tissue was the iVIEW™ SILVER (Ventana Medical Systems Product No. 790-098) detection system described herein. Briefly, a biotinylated HER2 gene probe (Ventana Medical Systems Product No. 780-2840) spanning the full coding sequence of the HER2 gene was hybridized using stringent, hybridization conditions to the HER2 gene in both normal and carcinoma tissues. Successively, an antibiotin rabbit polyclonal antibody, then a goat anti-rabbit-Horseradish Peroxidase conjugate antibody is incubated with the tissue. Prior to application of chromogenic reagents, slides were washed with an unbuffered solution containing a surfactant and water. Approximately 100 ul of the wash remains on the slide prior to reagent application, 100 ul each of Reagents A (0.18% silver acetate w/v), B (0.18% w/v hydroquinone in 0.1 M citrate buffer, pH 3.8), and C (0.07% hydrogen peroxide w/v), were dispensed onto the slide by the following protocol. Reagent A was applied first and incubated for 4 minutes at 37° C. Without rinsing, Reagent B was applied to the slide and allowed to incubate an additional 4 minutes at 37° C. Finally, Reagent C was added to the pool of Reagent A and B and incubated for a final 4 minutes at 37° C.

Figure 7:
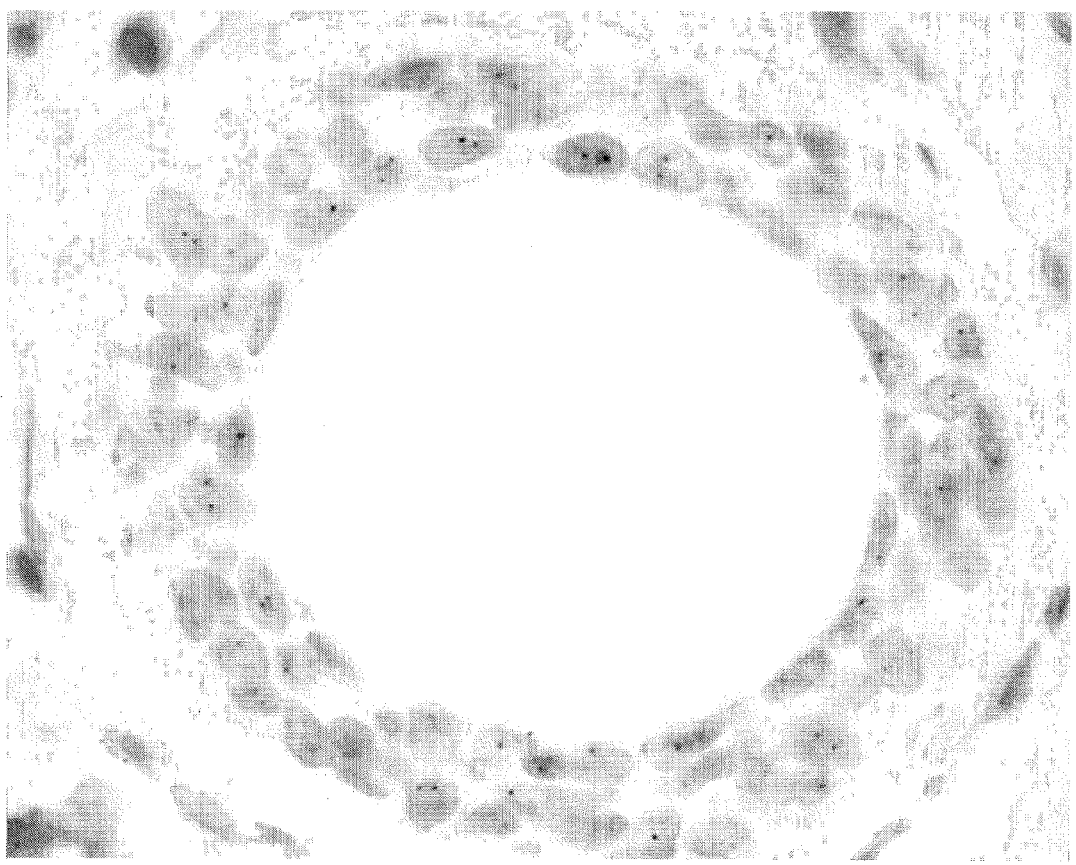
FIG. 7 is a photomicrograph at 100× showing dots of deposited silver metal as discrete single copies of HER2 gene in a 4 micron-section of normal breast duct tissue.

FIG. 7 is a photomicrograph at 100× showing dots of deposited silver metal as discrete single copies of HER2 gene in a 4 micron-section of normal breast duct tissue. There are one to two signals per cell, the normal complement. The tissue is counterstained violet with Hematoxylin II, a lipiphillic biological stain. Hematoxylin II stains cell nuclei violet through the binding of a mordant dye complex to nucleic acids and histone proteins of the heterochromatin (Ventana Medical Systems Product No. 790-2208) Bluing Reagent, a high pH metal salt and carbonate solution was applied to the tissue sample after rinsing and reacts with the Hematoxylin to produce a blue counterstain (Ventana Medical Systems Product No. 760-2037). Thus, FIG. 7 shows that by using the method of the present invention, a single copy of HER2 gene can be detected in normal breast tissue.

Figure 8:
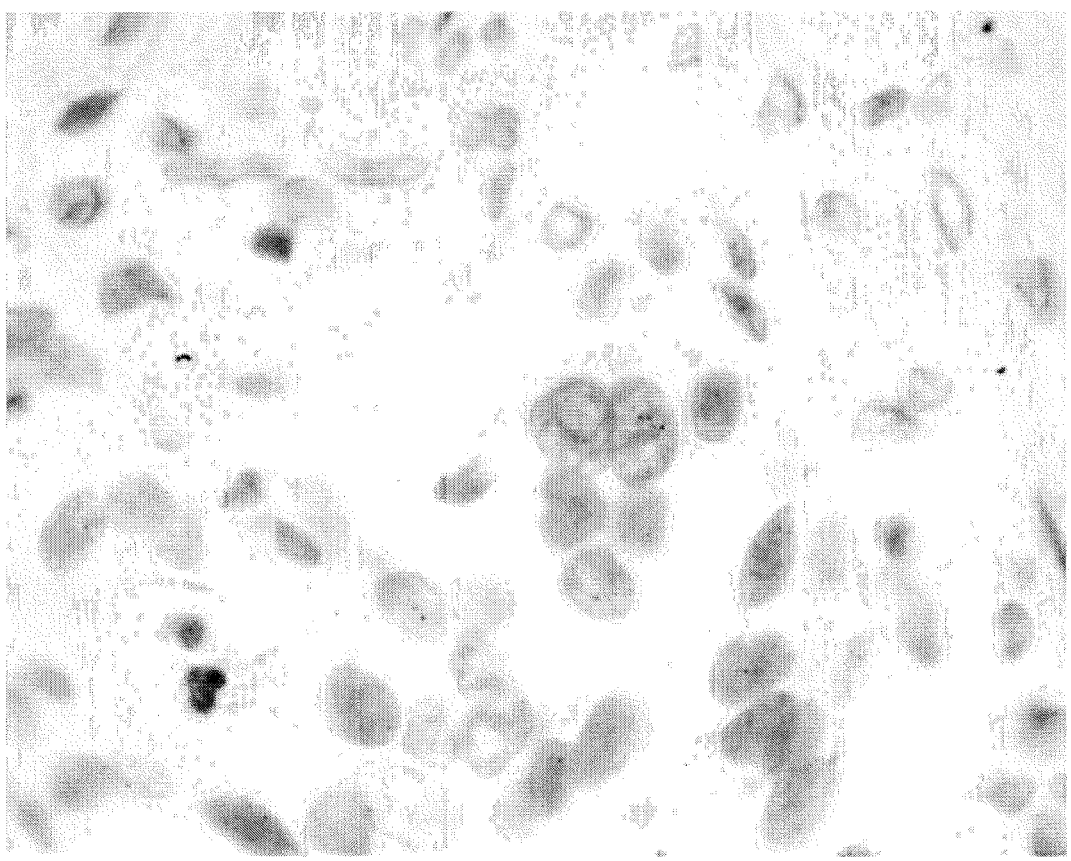
FIG. 8 is a photomicrograph at 100× showing dots of deposited silver metal as discrete single copies of HER2 gene in a 4 micron-section of breast tumor tissue that is not amplified for HER2.

FIG. 8 is a photomicrograph at 100× showing dots of deposited silver metal as discrete single copies of HER2 gene in a 4 micron-section of breast tumor tissue that is not amplified for HER2. As shown in FIG. 8, the normal complement of 2 single copies of the HER2 gene are readily distinguishable. Thus, FIG. 8 shows that by using the method of the present invention a single copy of HER2 gene can be detected in breast tumor tissue with non-amplified HER2 gene.

Figure 9:
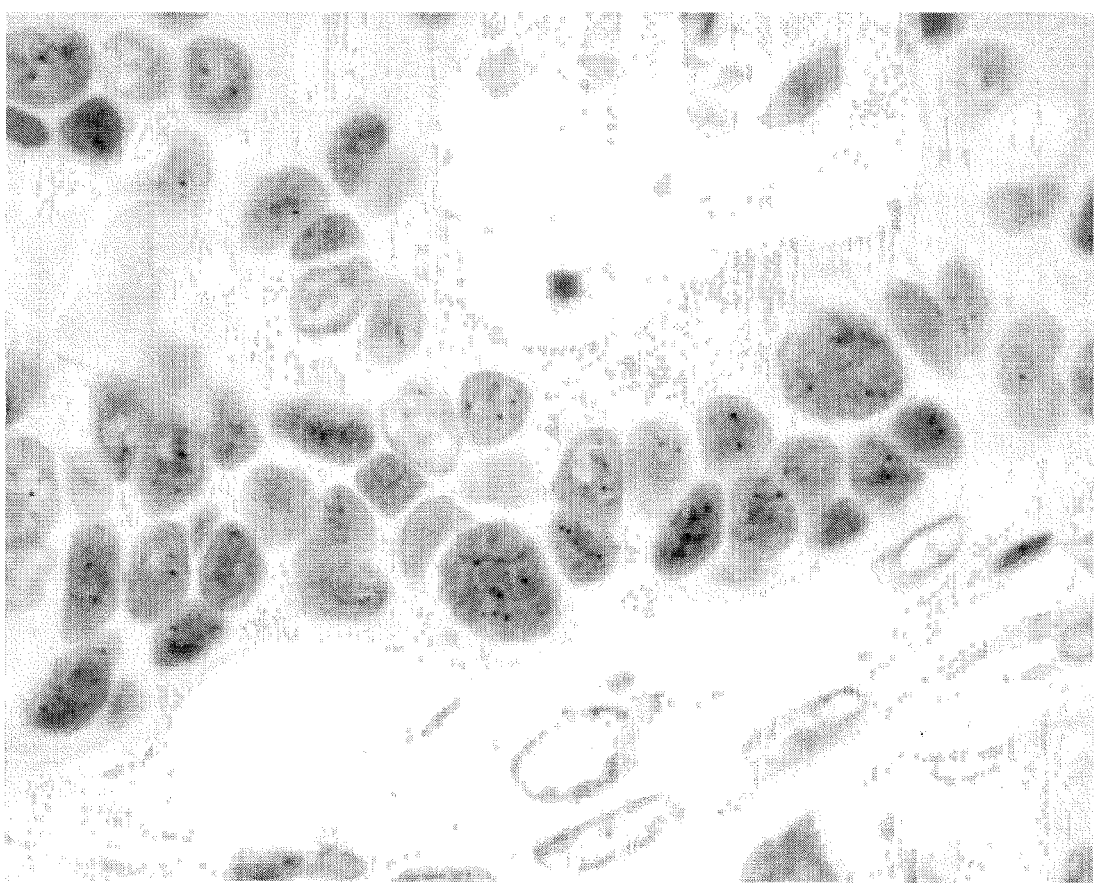
FIG. 9 is a photomicrograph at 100× showing dots of deposited silver metal as numerous copies of HER2 gene in a 4 micron-section of breast tumor tissue with low levels of HER2 gene amplification, from 3 to 5 copies of HER2 gene present in the tumor cells.

FIG. 9 is a photomicrograph at 100× showing dots of deposited silver metal as numerous copies of HER2 gene in a 4 micron-section of breast tumor tissue with low levels of HER2 gene amplification, from 3 to 5 copies of HER2 gene present in the tumor cells. Thus, FIG. 9 shows that by using the method of the present invention, multiple copies of HER2 gene can be detected in breast tumor tissue with low levels of HER2 gene amplification.

Figure 10:
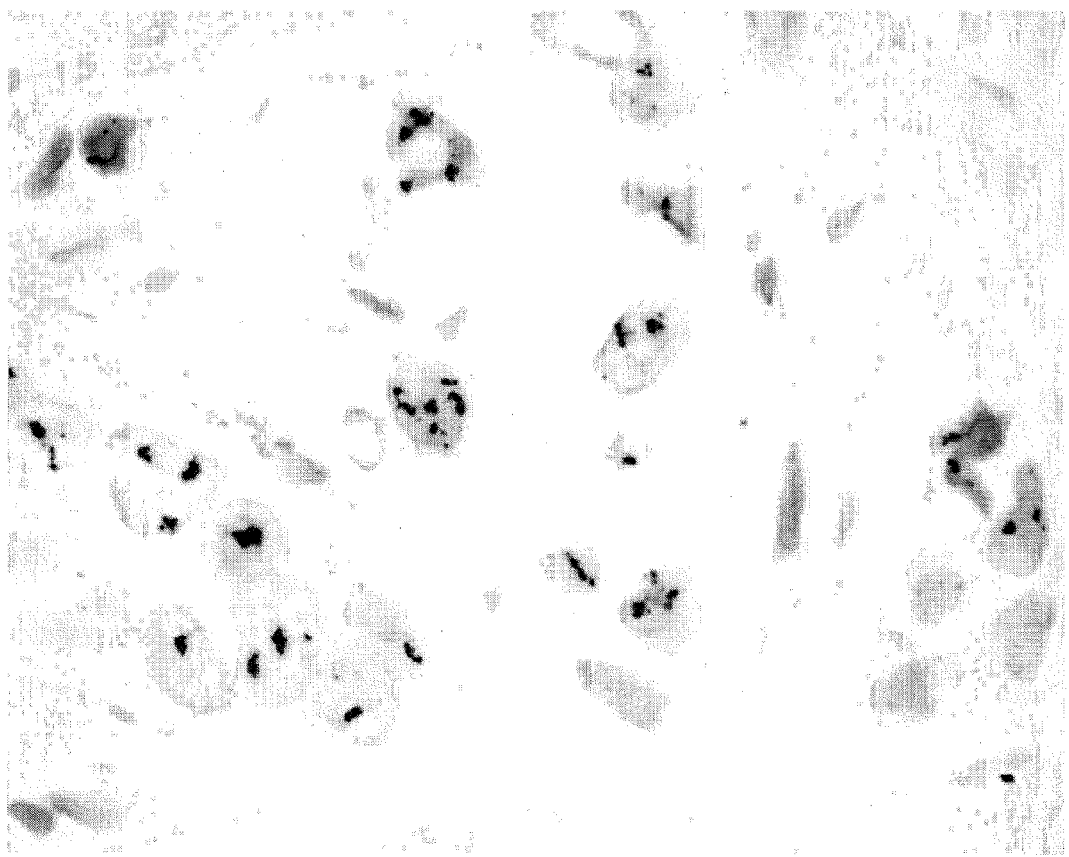
FIG. 10 is a photomicrograph at 100× showing dots of deposited silver metal as many copies of HER2 gene in a 4 micron-section of breast tumor tissue with relatively higher levels of HER2 gene amplification (than that of breast tumor tissue shown in FIG. 9), with 6 or greater copies of HER2 gene present in the tumor cells.

FIG. 10 is a photomicrograph at 100× showing dots of deposited silver metal as many copies of HER2 gene in a 4 micron-section of breast tumor tissue with relatively higher levels of HER2 gene amplification (than that of breast tumor tissue shown in FIG. 9), with 6 or greater copies of HER2 gene present in the tumor cells. Due to the high levels of HER2 gene amplification, the silver metal signals begin to become unresolved and appear to fuse into large clusters of silver metal. Thus, FIG. 10 shows that by using the method of the present invention, many copies of HER2 gene can be detected in breast tumor tissue with high levels of HER2 gene amplification and the size of the silver metal dots corresponds to the level of amplification of the targeted gene.

Figure 11:
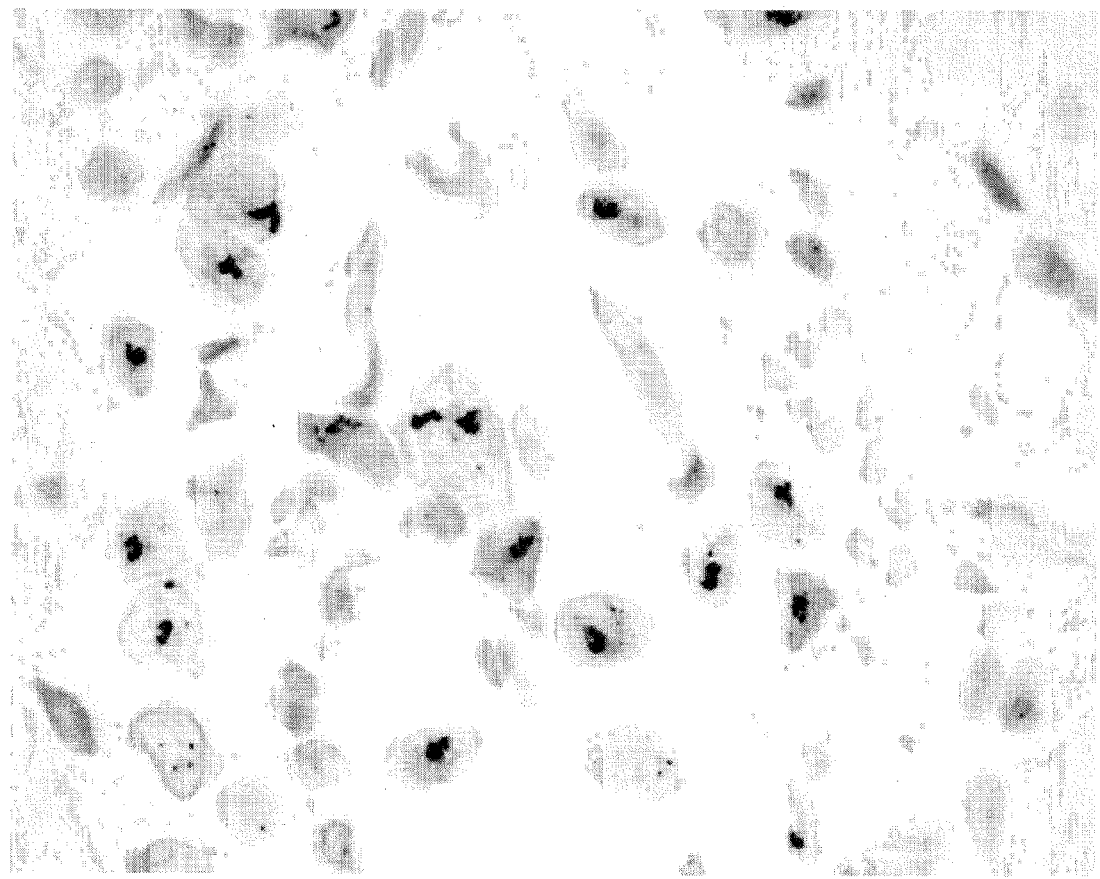
FIG. 11 is a photomicrograph at 100× showing dots of deposited silver metal as many copies of HER2 gene in a 4 micron-section of breast tumor tissue with even higher levels of HER2 gene amplification (than that of breast tumor tissue shown in FIG. 10).

FIG. 11 is a photomicrograph at 100× showing dots of deposited silver metal as many copies of HER2 gene in a 4 micron-section of breast tumor tissue with even higher levels of HER2 gene amplification (than that of breast tumor tissue shown in FIG. 10). Due to the extremely high level of HER2 gene amplification, the silver metal signal is so intense it becomes fused, forming a big dot of silver metal. This experiment further demonstrated that the method of the present invention can sensitively and selectively detect not only single copies of a targeted gene but also multiple copies of the targeted gene in situ; and the intensity of the metal signal corresponds to the level of amplification of the targeted gene.

In another experiment, the concentrations of the Reagent A, B and C and the silver staining reaction conditions were adjusted to further improve the sensitivity of the assay for detecting the gene copy of the HER2 gene and to further reduce the background staining. Briefly, a DNP (2,4-dinitrophenyl) labeled HER2 gene probe (Ventana Medical Systems Product No. 780-4332) was formulated in 80% Hybrizol containing 2 mg/ml Human DNA for use in assays. Silver in situ hybridization ("SISH") according to the present invention was performed on formalin-fixed, paraffin-embedded 4 micron-thick human breast tumor tissue sections mounted on glass microscope slides using the automated ISH protocol, available in conjunction with the BenchMark™ series instrument (Ventana Medical Systems, Tucson, Ariz.). In brief, after paraffin removal and protease treatments, hybridization with the DNP-labeled HER2 specific probe was carried out for 2 hours at 52° C. in 2×SSC and 23% formamide. After washing with 2×SSC a rabbit anti-DNP antibody (2 μg/ml) was applied, followed by a 20 minute incubation at 37° C. After washing, a goat HRP-conjugated anti-rabbit antibody was applied (15 μg/ml) and incubated for an additional 20 minutes. After washing with 100 mM citrate buffer pH 3.9, a solution of silver acetate (3.68 mg/ml) was applied and incubated for 4 minutes. It was washed again, and a second incubation with silver acetate (3.68 mg/ml)) was applied to the slide and incubated for 4 minutes. Without washing, a hydroquinone solution (1.78 mg/ml in 0.1 M citrate pH 3.8) of equal volume to that of the silver acetate solution was applied to the slide, followed by a solution of 0.09% w/v hydrogen peroxide of equal volume to that of the silver acetate solution, resulting in the final concentration of silver acetate being 1.23 mg/ml (or 0.123% w/v), hydroquinone 0.6 mg/ml (or 0.06% w/v), and 0.03% w/v hydrogen peroxide. After 12 minutes the slides were washed and dried for mounting. After silver staining, a nuclear counter stain (Hematoxylin, Ventana PN 790-2208) was applied, with bluing reagent (Ventana Medical Systems Product No. 760-2037) according to manufacturer's instructions.

Figure 12:
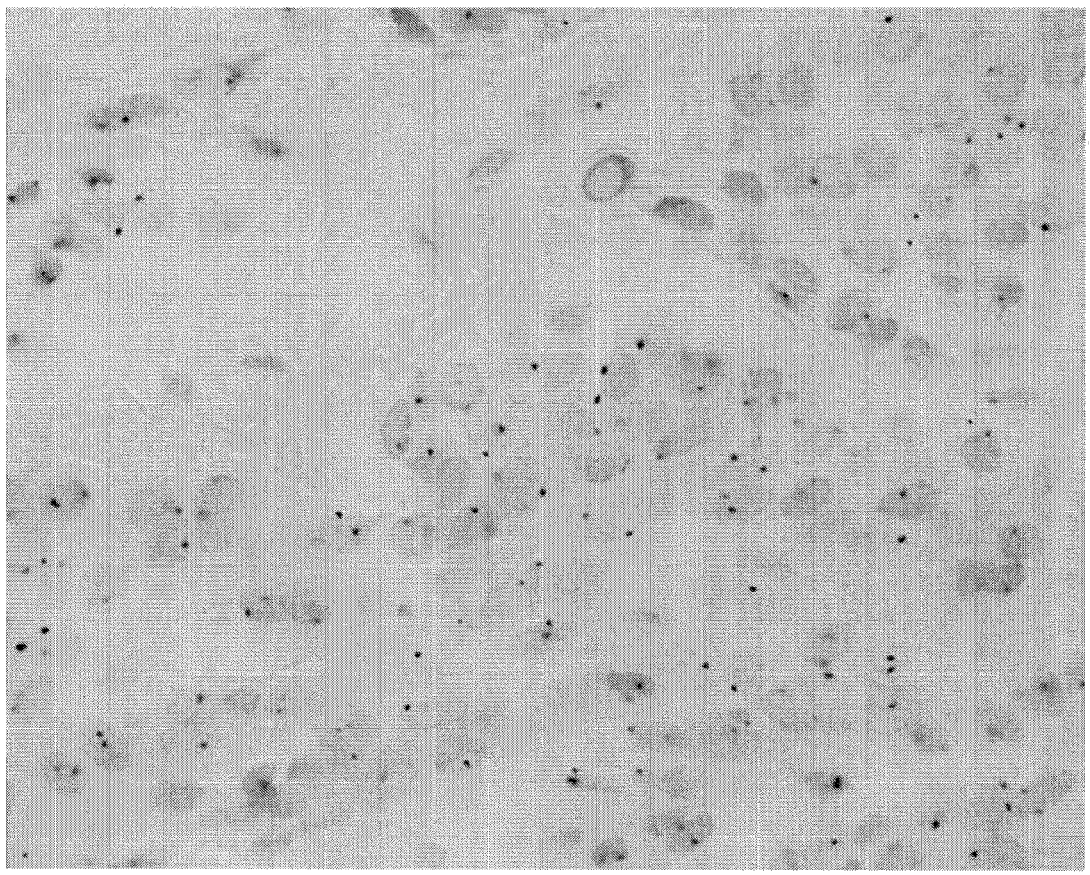
FIG. 12 is a photomicrograph showing dots of deposited silver metal as discrete single copies of HER2 gene in a breast tumor tissue that is not amplified for HER2.
Figure 13:
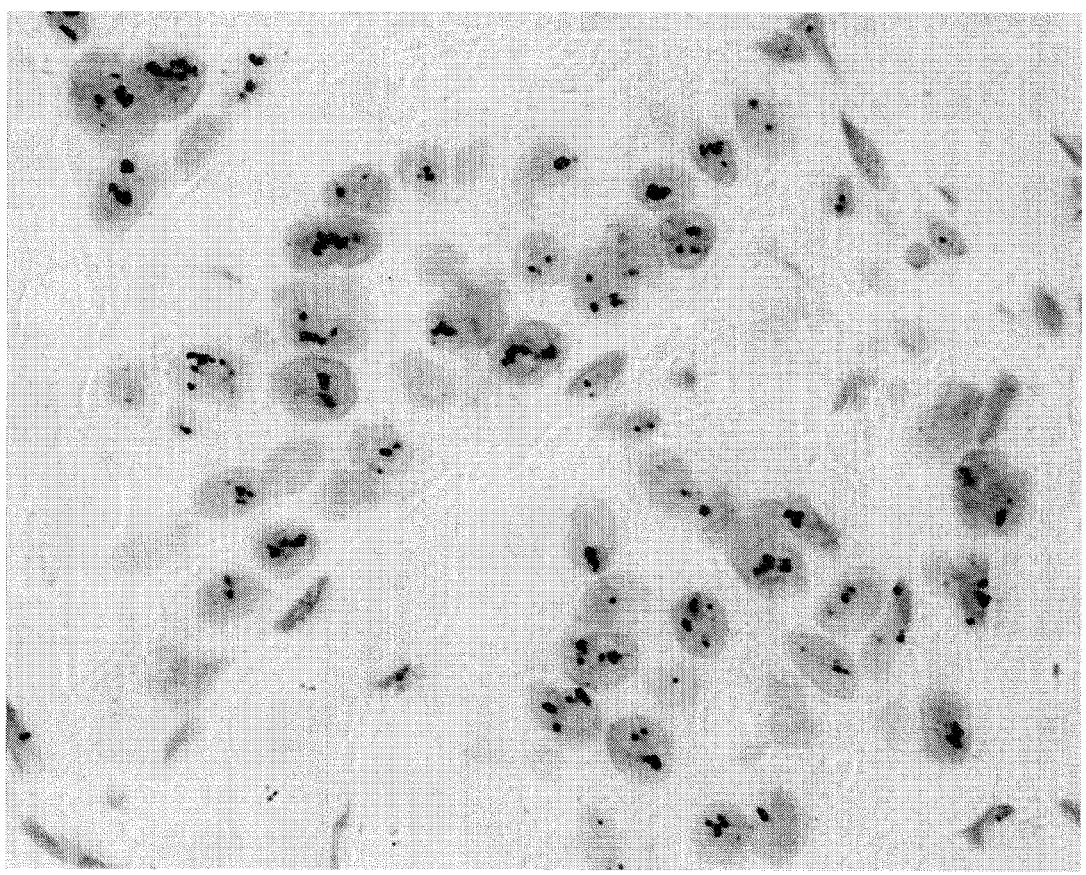
FIG. 13 is a photomicrograph showing dots of deposited silver metal as many copies of HER2 gene in a breast tumor tissue with relatively higher levels of HER2 gene amplification (than that of breast tumor tissue shown in FIG. 9), with 6 or greater copies of HER2 gene present in the tumor cells.

Exemplary SISH results are illustrated in FIGS. 12 and 13, which are lightfield photomicrographs. FIG. 12 shows a sample in which the HER2 target sequence is unamplified (diploid). Cells in this sample exhibit 2 or fewer hybridization signals (which appear as dark dots). FIG. 13 shows a sample in which the HER2 target sequence is amplified to many times the diploid copy number. Hybridization signals appear as a multifocal aggregates of black dots. Compared to FIG. 8, discrete single copies of HER2 gene shown in FIG. 12 are even more distinguishable with lower background levels.

Example 33

Mechanistic Studies and Optimization of Enzymatic Metal Deposition Assays of the Present Invention While not wishing to be bound to the theories described herein, the inventor conducted mechanistic studies of the enzymatic metal deposition and experiments on optimization of the reaction conditions.

According to the studies, the enzymatic metal deposition of the present invention is highly sensitive and specific. The metal deposition was observed to occur only at the enzyme sites or in the vicinity of the enzymes under optimized conditions. Adding the reaction components to a specific nucleic acid sequence-, or antigen-containing sample without enzyme labels, no specific staining was generated when the whole assay procedure is performed. Furthermore, no specific staining was observed if only metal ions and a reducing agent are added to enzyme labeled samples. Even if a reducing agent with an appropriate reduction potential of a half reaction is chosen, it can only chemically reduce the metal ions in the solution to metals to give nonspecific staining, but will not give any specific staining at the enzyme sites and in the vicinity of the enzyme. The inventor believes that in the enzymatic deposition process the enzymatic reactions reduce the metal ions to metals with the participation of both the reducing agent and oxidizing agent. The formed metals initiated further accumulation to provide detectable signals. For example, when horseradish peroxidase is combined with silver ions, e.g. silver acetate, and a reducing agent e.g. hydroquinone and an oxidizing agent e.g. hydrogen peroxide, silver metal deposits can form at the peroxidase site or in the vicinity of peroxidase. While not wishing to be bound to the mechanisms of action proposed herein, the inventor proposes the following three-step reaction cycle for the horseradish peroxidase oxidation of hydroquinone:

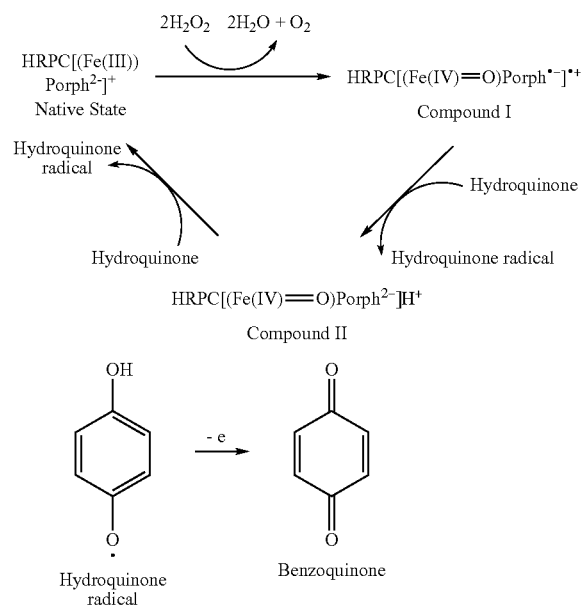

According to the hypothetical three-step cyclic reaction depicted above, the heme peroxidase is first oxidized by hydrogen peroxide to form the high oxidation state intermediate compound I which comprises an oxyferryl heme and a porphyrin cation radical. The net result of the step is the removal of two electrons from the heme system, Compound I reacts with the reducing substrate e.g. hydroquinone by extracting an electron and a proton from it. An additional single electron-transfer step returns the enzyme to the resting state by reaction with another reducing substrate. Peroxidase is known to catalyze the oxidation of a wide range of aromatic compounds, e.g. hydroquinone.

The electrons released from the heme in the formation of compound I can reduce the silver cations, which locate at the enzyme site or in the vicinity of the enzyme, into silver metals. Accumulation of several silver metal atoms e.g. Ag4 nucleates further silver deposition using the silver metal atoms formed from the solution chemical redox reaction between silver acetate and hydroquinone, generating detectable silver metal stains, as depicted in the following enzymatic silver deposition process:

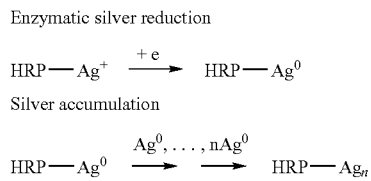

Both temperature and pH affect the enzymatic metal deposition reactions. The reactions can be performed in a wide range of temperatures, e.g. 0°-60° C. As the temperature increases, the reaction-rate generally increases, and to ensure reproducibility, a constant temperature should be employed. As a example, higher temperatures led to a rapid appearance of silver deposits in a peroxidase catalyzed silver deposition reaction, and shortened the deposition time to achieve certain signal intensity. However, as the temperature rises above the enzyme optimal temperature, hydrogen bonds are disrupted. This, in turn, may alter the shape of the enzyme so that its affinity for its substrate diminishes. The reaction rate therefore starts to decrease until at some high temperature all the enzymes are denatured and reactions cease. Furthermore, higher temperatures increase the risk of nonspecific metal deposition due to autocatalytic precipitation formed in developing solution specially when the deposition is prolonged beyond a certain time limit or temperature is kept too high.

The preferred pH for the enzymatic metal deposition of the present invention is controlled at low or near neutral pH, even though the enzyme may prefer at a different value, or its optimum pH (e.g. the optimum pH for peroxidase is 7.0). The low pH can help to achieve an even and symmetrical growth of the silver grains. The low pH can be achieved by using a pH controlled citrate buffer, acetate buffer or lactate buffer. Generally, the choice of the buffer is made by avoiding the formation of metal ion precipitate. For example, phosphate buffer is preferred not to be used in silver deposition because white silver phosphate precipitates out from the solution due to its low solubility product constant. Certain anions such as $Cl^-$, $Br^-$ and $I^-$ are preferred to be avoided in enzymatic silver deposition reaction for the same consideration. When tissue and cell samples are involved, thorough deionized water washes are preferred prior to applying the enzymatic metal deposition reaction components. The change of pH can significantly alter the metal deposition rate and intensity, and affect the sensitivity and nonspecific staining. Higher pH shortens the intensification time, but also favors the formation of nonspecific staining.

Figure 14:
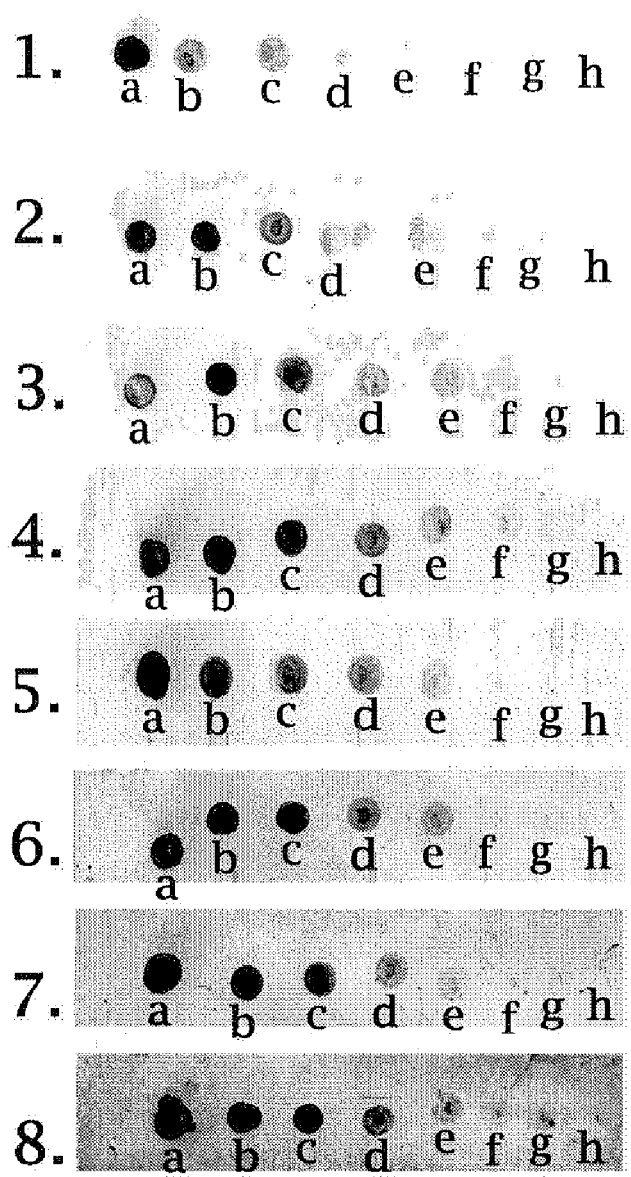
FIG. 14 shows dot immuno blots for detecting the sensitivity of the inventive enzymatic metal deposition assays at various concentrations of hydroquinone. (a) 10 ng; (b) 1 ng; (c) 0.5 ng; (d) 0.1 ng; (e) 0.05 ng; (f) 0.01 ng; (g) 0.005 ng; (h) 0.001 ng of rabbit IgG target antigen. (1) 0.025%; (2) 0.055%; (3) 0.059%; (4) 0.069%; (5) 0.084%; (6) 0.10%; (7) 0.13%; (8) 0.15% (w/v) final concentration of hydroquinone in the reagent mixture of hydroquinone, silver acetate and hydrogen peroxide. Final concentrations of 0.13% Silver acetate and 0.03% hydrogen peroxide were used in the reagent mixture of hydroquinone, silver acetate and hydrogen peroxide.

The concentrations of reaction components (weight/volume percentage in the reaction mix) and their addition sequences were found to affect the detection sensitivity, signal intensity, metal deposition rate as well as the nonspecific staining in quantitative dot-immuno-binding assays (such as those shown in FIG. 14). In a typical dot-immuno-binding assay, a series of different concentration of antigen solutions are blotted onto nitrocellulose membranes using an electronic pipettor. The membranes are blocked in a buffer containing carrier protein, e.g. bovine serum albumin, and detergent to prevent adventitious binding of antibodies. The membranes are then incubated in enzyme-labeled, e.g., horseradish peroxidase, antibody solution for a certain period of time, followed by rinses in a buffer, e.g. Tween 20-phosphate buffered saline and rinses in deionized water. Solutions of silver acetate, hydrogen peroxide, and hydroquninone buffered at an acidic pH are then added to the washed membranes simultaneously or in an order. The black, nonfading silver metal deposits appear over the area, where the antigens are applied, in a period from several seconds to several minutes depending on the applied antigen concentration. The membranes are then washed with water to stop the reaction.

The dot-immuno-binding studies found that the sensitivity (picograms of antigen detected) obtained by 0.12% silver acetate was ten fold higher than that offered by 0.038% silver acetate when 0.1% hydroquninone and 0.03% hydrogen peroxide are used. As the concentration of silver acetate increased, the silver deposit density of the dots with same antigen loading quantity increased, but plateaued when it reached 0.13%. The silver deposition rate was not significantly affected by the change of the concentration of silver ions. On the other hand, the nonspecific staining (evenly distributed over the surface of the membranes) increased as the concentration of silver ions increased (Table 1). However, the appearance of the nonspecific staining came after majority numbers of antigen loading dots were detected. If the metal deposition reaction is terminated prior to generation of nonspecific staining, a high signal-to-noise ratio can be achieved when an optimum concentrations of reagents are used.

TABLE 1

Sensitivity and non-specificity as functions of concentration of silver acetate in HRP-catalyzed silver deposition reaction

| | [Silver acetate], % (w/v) | | | | | | |
|---|---|---|---|---|---|---|---|
| | 0.038 | 0.067 | 0.10 | 0.12 | 0.13 | 0.15 | 0.23 |
| Sensitivity, picograms | 100 | 50 | 50 | 10 | 10 | 10 | 10 |
| Degree of nonspecific staining† | 0⁺ | + | ++⁺ | ++ | ++ | ++⁺ | +++ |

†Superscript note
⁺refers to a half level of background.

The detection sensitivity of the present method depends also on the concentration of the reducing agent used. For example, the increase of the concentrations of hydroquinone from 0.025% to 0.069% led to twenty fold higher sensitivity as shown by the dot-immuno-binding studies when silver acetate and hydrogen peroxide were used at 0.13% and 0.03% respectively (Table 2 and FIG. 3).

TABLE 2

Sensitivity and nonspecificity as functions of concentration of hydroquinone in HRP-catalyzed silver deposition reaction

| | [Hydroquinone], % (w/v) | | | | | | | |
|---|---|---|---|---|---|---|---|---|
| | 0.025 | 0.055 | 0.059 | 0.069 | 0.084 | 0.10 | 0.13 | 0.15 |
| Sensitivity, picograms | 100 | 50 | 10 | 5 | 5 | 5 | 5 | 5 |

TABLE 2-continued

Sensitivity and nonspecificity as functions of concentration of hydroquinone in HRP-catalyzed silver deposition reaction

| | [Hydroquinone], % (w/v) | | | | | | | |
|---|---|---|---|---|---|---|---|---|
| | 0.025 | 0.055 | 0.059 | 0.069 | 0.084 | 0.10 | 0.13 | 0.15 |
| Degree of nonspecific staining† | + | ++ | ++ | ++⁺ | ++⁺ | ++⁺ | +++ | +++⁺ |

†Superscript note
⁺refers to half level of background.

The sensitivity stayed the same as the concentration of hydroquinone was further increased from 0.069% to 0.15%. When the concentration of hydroquinone reached 0.25%, the formed silver deposits were later bleached away as the incubation prolonged beyond a certain time limit. The degree of nonspecific staining gradually rose as the concentration of hydroquinone increased. Again, most antigen spots were detected before nonspecific staining appeared. The metal deposition rate was not altered as the concentration of hydroquinone varied. However, the signal intensity at each antigen loading quantity was enhanced as the concentration of hydroquinone in the reaction mix increased.

A number of reducing agents can be used in the present method. Exemplary agents include hydroquinone, metol, bromohydroquinone, methoxyhydroquione and chlorohydroquinone. The reducing agent, protected against the light, is dissolved in low to neutral pH buffer by magnetic stirring. The solution may become brown in the air, due to oxidation, but this does not overtly affect its reducing power.

The concentration of the oxidizing agent is another factor which can affect the detection sensitivity. In HRP-catalyzed silver deposition reactions, the increase of the concentration of hydrogen peroxide in the reagent mixture improved the detection sensitivity, however, started to quench the peroxidase activity when it reached 0.23% when 0.1% silver acetate and 0.13% hydroquinone were used in the assays (Table 3). 3-5% hydrogen peroxide is normally sufficient to quench the endogenous peroxidase activity. However, a very low concentration of hydrogen peroxide is needed to have an effective enzymatic metal deposition reaction. Even 0% hydrogen peroxide could allow the observation of silver deposition, however, at much lower sensitivity. The use of a slightly higher concentration (e.g. still less than 0.23%) seems to help to remove the nonspecific staining caused by randomly binding of peroxidase-labeled antibodies or avidin-biotin complex. A concentration which might remove the specific staining should be avoided. The concentration of the oxidizing agent does not have a strong effect on the metal deposition rate and signal intensity over a certain range (Table 3) with the other conditions used.

TABLE 3

Sensitivity and nonspecificity as functions of concentration of hydrogen peroxide in HRP-catalyzed silver deposition reaction

| [$H_2O_2$], % (w/v) | 0.0038 | 0.0075 | 0.038 | 0.10 | 0.16 | 0.23 | 0.29 | 0.38 |
|---|---|---|---|---|---|---|---|---|
| Sensitivity, picograms | 10 | 10 | 5 | 10 | 10 | 50 | 50 | 100 |

TABLE 3-continued

Sensitivity and nonspecificity as functions of concentration of hydrogen peroxide in HRP-catalyzed silver deposition reaction

| [$H_2O_2$], % (w/v) | 0.0038 | 0.0075 | 0.038 | 0.10 | 0.16 | 0.23 | 0.29 | 0.38 |
|---|---|---|---|---|---|---|---|---|
| Degree of nonspecific staining† | +++ | ++++ | ++* | + | 0* | 0* | 0 | 0 |

†Superscript note
*refers to half level of background.

The reaction components can be applied to an enzyme-containing or -labeled target system simultaneously or in a particular order. However, the addition order and the time interval between the additions play a role in the enzymatic metal deposition reactions. One addition sequence can give better detection sensitivity and improved nonspecific staining than that obtained with another sequence. For example, the sequential addition of silver acetate, hydroquinone and hydrogen peroxide at four minute intervals provided five fold higher sensitivity than the addition order of silver acetate, hydrogen peroxide and hydroquinone with the same time interval. Although the sequential addition of silver acetate, hydrogen peroxide and hydroquinone was not as sensitive, it retarded the appearance of the nonspecific staining, and therefore the degree of the background appeared a lot lower for the same length of incubation. It was five fold more sensitive to apply silver acetate, hydroquinone and hydrogen peroxide in a sequential order with four minute intervals than to add silver acetate first and apply hydroquinone and hydrogen peroxide simultaneously in four minutes. The variation of the time interval affects the detection results as well.

The sensitivity of peroxidase-catalyzed metal deposition was further evaluated by testing combinations of different concentrations of reaction components designed on the basis of aforementioned findings (Table 4). The reaction mixture comprised of 0.12% silver acetate, 0.1% hydroquinone, and 0.03% hydrogen peroxide buffered at pH 4.16 (combination 3) added in that order gave the highest sensitivity. As little as 1 picogram IgG antigen could be detected on an immuno blot using this condition. Comparing with the assay conditions disclosed in Examples 5 and 6 above, the condition in combination 3 listed in Table 4 increased the detection sensitivity by fifty fold on dot-immuno-binding paper models. This sensitivity is at least ten fold higher than that obtained by immunogold detection in conjunction with silver or gold enhancement using the same study model. The much enhanced sensitivity provides means to achieve sensitive detection of protein or nucleic acid targets including single gene copy or low levels of gene expression.

TABLE 4

Sensitivity obtained with combinations of different concentration of silver acetate, hydroquinone and hydrogen peroxide

| Combination† | 1 | 2 | 3 | 4 | 5 |
|---|---|---|---|---|---|
| [Silver Acetate], % (w/v) | 0.067 | 0.10 | 0.12 | 0.13 | 0.15 |
| [Hydroquinone], % (w/v) | 0.17 | 0.13 | 0.10 | 0.083 | 0.063 |
| [$H_2O_2$], % (w/v) | 0.050 | 0.038 | 0.030 | 0.025 | 0.019 |
| Sensitivity (picograms) | 10 | 5 | 1 | 5 | 5 |

†Silver acetate, hydroquinone and hydrogen peroxide were added sequentially at four minute intervals.

The duration of the incubation in the reaction mixture, or developing time, determines the intensity of the staining. Depending on the abundance of the detection targets, thickness of the specimen, and preceding treatments, the incubation time may vary from several seconds to 15 minutes. Apparently, to achieve the highest detection level, the development may be carried out for longer times. This has, however, to be weighed against the degree of nonspecific staining. Excessive development can obscure cellular morphology, even in the absence of background staining.

The present method was further be modified with a post-development reduction step to reduce the nonspecific staining in either an overdeveloped section or blot or samples with unsatisfactory background staining. It was found that a brief rinse in 20% sodium thiosulfate plus 5% ammonium chloride, or 5% potassium thiocyanate, or 0.038% potassium ferricyanide plus 0.4% sodium thiosulfate, or 1.6% potassium ferricyanide, 2.5% sodium thiosulfate, or 1.1% sodium periodate was helpful in decreasing the nonspecific staining. However, careful monitoring of the background reduction is preferred to avoid removing specific staining.

Details of the experiments in this example are described as follows.

1) Sensitive Detection of Antigens in Dot-Immuno-Binding Assay

One microliter aliquots of 0.01, 0.001, 0.0005, 0.0001, 0.00005, 0.00001, 0.000005, and 0.000001 mg/ml rabbit IgG were spotted onto 0.20 μm nitrocellulose membrane using an electronic pipettor (0-10 μl), yielding 10, 1, 0.5, 0.1, 0.05, 0.01, 0.005, 0.001 ng loading of antigen per dot, respectively. Application of samples resulted in circular spots with 0.25 cm in diameter. The membrane was air-dried for 30 minutes, and rehydrated in 20 mM sodium phosphate buffer pH 7.4 containing 150 mM sodium chloride and 0.1% (w/v) Tween 20 (PBST). The membrane was blocked by immersion in 5% (w/v) bovine serum albumin in Tween 20-phosphate-buffered saline (PBST) for 30 minutes at room temperature. The membrane was then incubated in anti-rabbit IgG horseradish peroxidase conjugate in 1:400 dilution in 1% (w/v) bovine serum albumin in Tween 20-phospbate-buffered saline (PBST) for 2 hours at room temperature with agitation. The membrane was rinsed three times in PBST for 5 minutes each time, and then followed by three 5 minutes rinses in deionized water. All rinses were performed under agitation. The membrane was exposed to the inventive enzymatic metal deposition reagent mixture containing 0.12% silver acetate, 0.1% hydroquinone, and 0.03% hydrogen peroxide buffered at pH 4.16 added in that order at 4 minute intervals. After 15 minutes, the incubation was stopped by three consecutive 3 minute washes in deionized water. The black dots with 10, 1, 0.5, 0.1, 0.05, and 0.01 ng of antigen loading appeared in less than three minute of incubation time. A light grey color evenly distributed over the membrane started to appear after 10 minute of incubation.

At the end of the incubation, all eight dots were clearly seen, yielding a sensitivity of 1 picogram of detected IgG target.

2) Concentration of Silver Acetate

The experimental procedure described in section 1) above was used except that different concentrations of silver acetate were tested and compared. Silver acetate was added and mixed to a final concentration (w/v) of 0.038%, 0.067%, 0.10%, 0.12%, 0.13%, 0.15% and 0.23% when 0.1% hydroquinone and 0.03% hydrogen peroxide were used. The lowest loading quantity of rabbit IgG which can be clearly seen with these concentrations of silver acetate were 100, 50, 50, 10, 10, 10 and 10 picograms, respectively. The time when the dots of same rabbit IgG loading quantity appeared was not significantly different among those tested silver acetate concentrations. However, the black silver deposit density of the dots with same rabbit IgG loading quantity increased as the concentration of silver acetate was raised from 0.038% to 0.13%, and stayed unchanged when the concentration was further increased from 0.13% to 0.23%. The membrane background increased as the concentration of silver acetate increased from 0.038% to 0.23%.

3) Concentration of Hydroquinone

The experimental procedure described in section 1) above was followed except that the concentration of hydroquinone was varied and compared. Hydroquinone was used at a final concentration of 0.025%, 0.055%, 0.059%, 0.069%, 0.084%, 0.10%, 0.13% and 0.15%, along with 0.13% silver acetate and 0.03% hydrogen peroxide, and the results of the dot-immuno-binding assay are shown in FIG. 14. As shown in FIG. 14, with the sequential addition of silver acetate, hydroquinone and hydrogen peroxide at 4 minute intervals, the lowest visible amount of rabbit IgG target antigen loaded onto membranes decreased as the concentration of hydroquinone increased from 0.025% to 0.069%, and plateaued when concentrations were higher than 0.069%. The level of background on membranes increased as the concentration of hydroquinone increased. The dots with the loaded amount of rabbit IgG higher than 50 picograms were seen within 3 minutes of incubation time.

4) Concentration of Hydrogen Peroxide

The enzymatic metal deposition reagent mixtures containing 0%, 0.0038%, 0.0075%, 0.038%, 0.10%, 0.16%, 0.23%, 0.29% and 0.38% of hydrogen peroxide along with 0.10% silver acetate and 0.13% hydroquinone were evaluated using the same procedure of described in section 1) above. The sequential addition of silver acetate, hydroquinone and hydrogen peroxide at 4 minute intervals was used in the assays. The increase of the hydrogen peroxide concentration from 0.0038% to 0.038% resulted in an increase of sensitivity from 10 to 5 picograms. Further increase of the concentration to 0:10% and 0.16% did not further advance the sensitivity. When 0.23%, 0.29% and 0.38% hydrogen peroxide were used, the sensitivity dropped to 50, 50, 100 picograms, respectively. Surprisingly, 0% hydrogen peroxide also allowed the observation of silver deposition, however, at much lower sensitivity. The level of background decreased as the concentration of hydrogen peroxide increased within the range tested.

5) Order of Addition of Reaction Components

A series of rabbit IgG target solutions was spotted onto 0.2 μm nitrocellulose membranes, resulting in circular spots of 0.25 cm in diameter with 10, 1, 0.5, 0.1, 0.05, 0.01, 0.005, and 0.001 ng spots of IgG. The membranes were allowed to air dry for 30 minutes. After immersion in Tween 20-phosphate-buffered saline (PBST) for 5 minutes, the membranes were blocked by 5% (w/v) bovine serum albumin in Tween 20-phosphate-buffered saline (PBST) for 30 minutes at room temperature. Membranes were then incubated in horseradish peroxidase attached anti-rabbit IgG primary antibody which had been diluted in 1:400 dilution with a solution of 1% (w/v) bovine serum albumin in Tween 20-phosphate-buffered saline (PBST) for 2 hours at room temperature with agitation. This was followed by three 5 minutes rinses in PBST and three 5 minutes rinses in deionized water with agitation. The membranes were treated with the enzymatic metal deposition reagent mixture containing 0.1% silver acetate, 0.13% hydroquinone and 0.038% hydrogen peroxide buffered at pH 4.16. To one membrane, hydroquinone and hydrogen peroxide were added simultaneously at 4 minutes after silver acetate was added. After 15 minutes of incubation, the lowest amount of antigen detected was 50 picograms. For the membrane which was exposed to the sequential addition of silver acetate, hydroquinone and hydrogen peroxide at 4 minute intervals, the lowest amount of antigen detected was 5 picograms. The sequential addition of silver acetate, hydrogen peroxide and hydroquinone at 4 minute intervals resulted in 10 picograms of detection sensitivity but with less background.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A kit for depositing a metal comprising:
    metal ions selected from the group consisting of silver, gold, iron, mercury, nickel, copper, platinum, palladium cobalt, iridium ions and a mixture thereof;
    an oxidizing agent;
    a reducing agent; and
    an enzyme,
    wherein the weight ratio of the metal ions to the reducing agent ranges from 1:5 to 5:1, and the weight ratio of the reducing agent to the oxidizing agent ranges from 1:10 to 10:1.

2. The kit of claim 1, further comprising: a binding moiety that binds to a target molecule.

3. The kit of claim 2, wherein the binding moiety is selected from the group consisting of antibody, antibody fragments, peptide, nucleic acids, nucleic acid probes and synthetic molecules.

4. The kit of claim 3, wherein the target molecule is a target gene or genome and the binding moiety is a nucleic acid probe that binds to the target gene or genome.

5. The kit of claim 3, wherein the enzyme binds to the target molecule via a primary antibody that binds to the target molecule, or via a primary antibody that binds to the binding moiety.

6. The kit of claim 5, wherein the enzyme is conjugated to a secondary antibody that binds to the primary antibody.

7. The kit of claim 1, wherein the enzyme is peroxidase; the metal ions are silver ion; the oxidizing agent is hydrogen peroxide; and the reducing agent is hydroquinone.

8. The kit of claim 1, further comprising: instruction for performing a process of depositing elemental metal in the vicinity of the enzyme.

9. The kit of claim 2, wherein the target molecule is a gene encoding or a gene product of an angiogenic growth factor receptor selected from the group consisting of receptor for fibrin (VE-cadherin), receptors for VEGF (Flt1 and KDR), receptor for VEGF-C and VEGF-D (Flt4), receptor for VEGF-165 (NP-1 and NP-2), receptors for angiopoeitin-1, -2, -3, and -4 (Tie1 and Tie 2), receptors for FGF (FGF-R1, -R2, -R3, and -R4), receptor for PDGF (PDGF-R), receptor for ephrine A1-5 (Eph A1-8), and receptor for ephrine B1-5 (Eph B1-8).

10. The kit of claim 2, wherein the target molecule is a gene encoding or a gene product of a receptor tyrosine kinase selected from the group consisting of epidermal growth factor receptors (EGFR), plateley-derived growth factor receptors (PDGFR), vascular endothelial growth factor receptors (VEGFR), nerve growth factor receptors (NGFR), fibroblast growth factor receptors (FGFR), insulin receptors, ephrin receptors, Met, and Ror.

11. The kit of claim 10, wherein the epidermal growth factor receptor is HER1, HER2/new (or HER2/new), HER3, or HER4.

12. The kit of claim 2, wherein the target molecule is a gene encoding or a gene product of a non-receptor tyrosine kinase selected from the group consisting of Kit, Src, Fes, JAK, Fak, Btk, Syk/ZAP-70, and Abl.

13. The kit of claim 12, wherein the Kit is c-Kit.

14. A kit for depositing a metal, comprising:
metal ions selected from silver, gold, iron, mercury, nickel, copper, platinum, palladium cobalt, iridium ions and mixtures thereof;
an oxidizing agent;
a reducing agent;
an enzyme; and
a binding moiety that binds to a target molecule, the binding moiety being selected from an antibody, an antibody fragment, a peptide, a nucleic acid, a nucleic acid probe, and a synthetic molecule,
wherein the weight ratio of the metal ions to the reducing agent ranges from 1:5 to 5:1, and the weight ratio of the reducing agent to the oxidizing agent ranges from 1:10 to 10:1.

\* \* \* \* \*